United States Patent [19]
Godiska et al.

[11] Patent Number: 5,932,703
[45] Date of Patent: *Aug. 3, 1999

[54] MACROPHAGE DERIVED CHEMOKINE AND CHEMOKINE ANALOGS

[75] Inventors: Ronald Godiska, Bothell; Patrick W. Gray, Seattle, both of Wash.

[73] Assignee: ICOS Corporation, Bothell, Wash.

[21] Appl. No.: 08/660,542

[22] Filed: Jun. 7, 1996

Related U.S. Application Data

[63] Continuation-in-part of application No. 08/558,658, Nov. 16, 1995, which is a continuation-in-part of application No. 08/479,620, Jun. 7, 1995.

[51] Int. Cl.$^6$ .......................... C07K 14/52; A61K 38/19
[52] U.S. Cl. .......................... 530/351; 530/324; 930/140; 424/85.1
[58] Field of Search .................................. 530/351, 324; 930/140; 424/85.1

[56] References Cited

U.S. PATENT DOCUMENTS

| | | | |
|---|---|---|---|
| 4,965,392 | 10/1990 | Fritzberg et al. | 558/254 |
| 5,037,630 | 8/1991 | Fritzberg et al. | 424/1.1 |
| 5,179,078 | 1/1993 | Rollins et al. | 514/2 |
| 5,241,049 | 8/1993 | Goodman et al. | 530/350 |
| 5,278,287 | 1/1994 | Rollins et al. | 530/351 |
| 5,413,778 | 5/1995 | Kunkel et al. | 424/1.41 |

FOREIGN PATENT DOCUMENTS

| | | |
|---|---|---|
| 0 310 136 | 4/1989 | European Pat. Off. . |
| WO 95/13295 | 5/1995 | WIPO . |
| WO 95/17092 | 6/1995 | WIPO . |

OTHER PUBLICATIONS

Adams, D.O., "The Granulomatous Inflammatory Response," *Am. J. Pathol.*, 84(1):164–191 (Jul., 1976).
Ahuja et al., "Molecular Evolution of the Human Interleukin–8 Receptor Gene Cluster," *Nature Genetics*, 2:31–36 (Sep., 1992).
Altschul et al., "Basic Local Alignment Search Tool," *J. Mol. Biol.*, 215: 403–410 (1990).
Baggioloni et al., "Interleukin–8 and Related Chemotactic Cytokines–CXC and CC Chemokines," *Advances in Immunology*, 55:97–179 (1994).
Becker et al., "Constitutive and stimulated MCP–1, GROα, β, and γ expression in human airway epithelium and bronchaolveolar macrophages," *Am. J. Physiol.*, 266:L278–L288 (1994).
Better et al., "*Escherichia coli* Secretion of an Active Chimeric Antibody Fragment," *Science*, 240:1041–1043 (May 20, 1988).
Bitter et al., "Secretion of Foreign Proteins from *Saccharomyces cerevisiae* directed by α–factor gene fusions," *Proc. Nat'l. Acad. Sci., USA*, 81:5330–5334 (Sep., 1984).
Bowie et al., "Deciphering the Message in Protein Sequences: Tolerance to Amino Acid Substitutions," *Science*, 247:1306–1310 (1990).
Brown et al., "A Family of Small Inducible Proteins Secreted by Leukocytes are Members of a New Superfamily that Includes Leukocyte and Fibroblast–Derived Inflammatory Agents, Growth Factors, and Indicators of Various Activation Process," *J. Immunol.*, 142(2):679–687 (Jan. 15, 1989).
Chang, "Thrombin Specificity: Requirement For Apolar Amino Acids Adjacent to the Thrombin Cleavage Site of Polypeptide Substrate," *Eur. J. Biochem.*, 151:217–224 (1985).
Chang et al., "Cloning and expression of a γ–interferon–inducible gene in monocytes: a new member of a cytokine gene family," *International Immunology*, 1(4):388–397 (1989).
Charo et al., "Molecular cloning and functional expression of two monocyte chemmoattractant protein 1 receptors reveals alternative splicing of the carboxyl–terminal tails," *Proc. Nat'l. Acad. Sci., USA*, 91:2752–2756 (Mar., 1994).
Chemokines, in R&D Systems 1995 catalog, R&D Systems, Minneapolis, MN, pp. 79–85.
Chen et al., "Calcium Phosphate–Medicated Gene Transfer: A Highly Efficient Transfection System for Stably Transforming Cells with Plasmid DNA," *BioTechniques*, 6(7):632–638 (1988).
Chen et al., "High–Efficiency Transformation of Mammalian Cells by Plasmid DNA," *Mol. Cell. Biol.*, 7(8):2745–2752 (Aug., 1987).
Cheung et al., "Modulation of Lymphocyte Motility by Macrophages," *Cell. Immunol.*, 109(2):295–305 (1987).
Clark–Lewis et al., "Structure–Activity Relationships of Interleukin–8 Determined Using Chemically Synthesized Analogs," *J. Biol. Chem.*, 266(34):23128–23134 (Dec. 5, 1991).

(List continued on next page.)

*Primary Examiner*—Garnette D. Draper
*Attorney, Agent, or Firm*—Marshall, O'Toole, Gerstein, Murray & Borun

[57] ABSTRACT

The present invention provides purified and isolated polynucleotide sequences encoding a novel human macrophage-derived C—C chemokine designated MDC, and polypeptide analogs thereof. Also provided are materials and methods for the recombinant production of the chemokine, and purified and isolated chemokine protein, and polypeptide analogs thereof.

5 Claims, 8 Drawing Sheets

OTHER PUBLICATIONS

Cocchi et al., "Identification of Rantes, MIP–1α, and MIP–1β as the Major HIV–Suppressive Factors Produced by CD8+ T Cells," *Science*, 270:1811–1815 (Dec. 15, 1995).

Combadiere et al., "Cloning and Functional Expression of a Human Eosinophil CC Chemokine Receptor," *J. Biol. Chem.*, 270(27):16491–16494 (Jul. 14, 1995).

Daly et al., "High Activity Suppression of Myeloid Progenitor Proliferation by Chimeric Mutants of Interleukin 8 and Platelet Factor 4," *J. Biol. Chem.*, 270(40):23282–23292 (Oct. 6, 1995).

Danoff et al., "Cloning, Genomic Organization, and Chromosomal Localization of the Scya5 Gene Encoding the Murine Chemokine Rantes," *J. Immunol.*, 152:1182–1189 (1994).

Denholm et al., "Changes in the Expression of MCP–1 Receptors on Monocyte THP–1 Cells Following Differentiation to Macrophages with Phorbol Myristate Acetate," *Cytokine*, 7(5):436–440 (Jul., 1995).

Denholm et al., "Differential Effects of Two Fluorescent Probes on Macrophage Migration as Assessed by Manual and Automated Methods," *Cytometry*, 19:366–369 (1995).

Denholm et al., "Monocyte Chemoattractants in Pigeon Aortic Atherosclerosis," *Amer. J. Pathol.*, 126:464–475 (1987).

Denholm et al., "Secretion of Monocyte Chemotactic Activity by Alveolar Macrophages," *Amer. J. Pathol.*, 135(3):571–580 (Sep., 1989).

Denholm et al., "The Effects of Bleomycin on Alveolar Macrophage Growth Factor Secretion," *Amer. J. Pathol.*, 134(2):355–363 (Feb., 1989).

Devergne et al., Production of the Rantes Chemokine by Macrophages and Endothelial Cells in Delayed–Type Hypersensitivity Reactions, *Challenges Mod. Med.*, 8:59–62 (1994).

Devi et al., "Biologic Activities of the beta–chemokine TCA3 on neutrophils and macrophages," *J. Immunol.*, 154(10):5376–5383 (1995).

Driscoll, K.E., "Macrophage Inflammatory Proteins: Biology and Role in Pulmonary Inflammation," *Exp. Lung Res.*, 20(6):473–490 (1994).

Dunlop et al., "Demonstration of Stem Cell Inhibition and Myeloprotective Effects of SCI/rhMIP1α In Vivo," *Blood*, 79(9):2221–2225 (May 1, 1992).

Elstad et al., "Synthesis and Release of Platelet–Activating Factor by Stimulated Human Mononuclear Phagocytes," *J. Immunol.*, 140(5):1618–1624 (Mar. 1, 1988).

Falk et al., "Specificity and Reversibility of Chemotactic Deactivation of Human Monocytes," *Infection and Immunity*, 32(2):464–468 (May, 1981).

Fowlkes et al., "Multipurpose Vectors for Peptide Expression on the M13 Viral Surface," *BioTechniques*, 13(3):422–427 (1992).

Frömmel et al., "An Estimate on the Effect of Point Mutation and Natural Selection of the Rate of Amino Acid Replacement in Proteins," *J. Mol. Evol.*, 21:233–257 (1985).

Gao et al., "Structure and Functional Expression of the Human Macrophage Inflammatory Protein 1α/Rantes Receptor," *J. Exp. Med.*, 177:1421–1427 (May, 1993).

Gerard et al., "Human Chemotaxis Receptor Genes Cluster at 19q13.3–13.4 Characterization of the Human C5a Receptor Gene," *Biochemistry*, 32:1243–1250 (1993).

Goodwin et al., "the 3'–Flanking Sequence of the Bovine Growth Hormone Gene Contains Novel Elements Required for Efficient and Accurate Polyadenylation," *J. Biol. Chem.*, 267(23):16330–16334 (Aug. 15, 1992).

Gray, "Inflammatory Bowel Disease," *in Scientific American Medicine*, Dale & Federman, (Eds.), New York, Scientific American, Inc., vol. 1, Chapter 4, Part IV, pp. 10–16 (1991).

Harada et al., "Essential Involvement of Interleukin–8 (IL–8) in acute inflammation," *J. Leukocyte Biology*, 56:559–564 (Nov., 1994).

Hayashi et al., "Production and function of monocyte chemoattractant protein–1 and other β–chemokine in murine glial cells," *J. Neuroimmunol.*, 60(1–2):143–150 (1995).

Holmes et al., Structure and Functional Expression of a Human Interleukin–8 Receptor, *Science*, 253:1278–1280 (Sep. 13, 1991).

Horuk et al., "Purification, Receptor, Binding Analysis, and Biological Characterization of Human Melanoma Growth Stimulating Activity (MGSA)," *J. Biol. Chem.*, 268(1):541–546 (Jan. 5, 1993).

Howard et al., "Chemokines: progress toward identifying molelcular targets for therapuetic agents," *TIBTECH*, 14(2):46–51 (1996).

In Vitro Assays of Lymphocyte Functions, in *Current Protocols Immunology*, Sections 3–4, Wiley and Sons (1992).

Kelvin et al., "Chemokines and Serpentines: The Molecular Biology of Chemokine Receptors," *J. Leukocyte Biology*, 54:604–612 (Dec., 1993).

Kuna et al., "Rantes, a Monocyte and T Lymphocyte Chemotactic Cytokine Releases Histamine from Human Basophils," *J. Immunology*, 149(2):636–642 (Jul. 15, 1993).

Kurjan et al., "Structure of a Yeast Peromone Gene (MFα): A Putative α–Factor Precurson Contains Four Tandem Copies of Mature α–Factor," *Cell*, 30:933–943 (Oct., 1982).

Laning et al., "Inhibition of In Vivo Tumor Growth by the β Chemokine, TCA3," *J. Immunology*, 153:4625–4635 (1994).

Luo et al., Biologic Activities of the murine β–Chemokine TCA3, *J. Immunology*, 153:4616–4624 (1994).

Major and Hamilton, "Oxidized LDL Selectively Potentiates LPS–Induced Chemokine mRNA Expression in Murine Peritoneal Macrophages," Thirty–first National Meeting of the Society for Leukocyte Biology on Host Devense Against Infections and Cancer, Marco Island, Florida, USA, Sep. 13–16, 1995. *Journal of Leukocyte Biology, O(Supplement)*:14 (1995) (Abstract 47).

Malden et al., "The Influence of Oxidatively Modified Low Density Lipoproteins on Expression of Platelet–derived Growth Factor by Human Monocyte–derived Macrophages," *J. Biol. Chem*, 266(21):13901–13907 (Jul. 25, 1991).

Matsushima et al., "Purification and Characterization of a Novel Monocyte Chemotactic and Activating Factor Produced by a Human Myelomonocytic Cell Line," *J. Exp. Med.*, 169:1485–1490 (Apr. 1989).

Maze et al., "Myelosuppressive Effects in Vivo of Purified Recombinant Murine Macrophage Inflammatory Protein–1α," *J. Immunol.*, 149(3):1004–1009 (Aug. 1, 1992).

Merrifield, R.B., "Solid Phase Peptide Synthesis. I. The Synthesis of a Tetrapeptide," *J. Am. Chem. Soc.*, 85:2149–2154 (Jul. 20, 1963).

Meurer et al., "Formation of Eosinophilic and Monocytic Intradermal Inflammatory Sites in the Dog by Injection of Human Rantes but not Human Monocyte Chemoattractant Protein 1, Human Macrophage Inflammatory Protein 1α, or Human Interleukin 8," *J. Exp. Med.*, 178:1913–1921 (Dec., 1993).

Miller et al., "A Novel Polypeptide Secreted by Activated Human T Lymphocytes," *J. Immunology*, 143(9):2907–2916 (Nov. 1, 1989).

Murphy et al., "Cloning of Complimentary DNA Encoding a Functional Human Interleukin–8 Receptor," *Science*, 253:1280–1283 (Sep. 13, 1991).

Nakao et al., "Structures of Human Genes Coding for Cytokine LD78 and Their Expression," *Mol. Cell. Biol.*, 10(7):3646–3658 (Jul., 1990).

Nakogawa et al., "Cytokine–Induced Neutrophil Chemoattractant (CINC)–2 α, a Novel Member of Rat GRO/CINCs, Is a Predominant Chemokine Produced by Lipopolysaccharide–Stimulated Rat Macrophages in Culture," *Biochem. Biophys. Res. Commun.*, 220(3):945–948 (1996).

Neote et al., Molecular Cloning, Functional Expression, and Signaling Characteristics of a C–C Chemokine Receptor, *Cell*, 72:415–425 (Feb. 12, 1993).

Ngo et al., "Computational Complexity, Protein Structure Prediction, and the Levinthal Paradox," *The Protein Folding Problem and Tertiary Structure Prediction*, K. Merz, Jr. and S. Le Grand, Editors, Birkhäuser Boston, pp. 433 and 492–495 (1994).

Peri et al., "A new monoclonal antibody (5D3–F7) which recognizes human monocyte–chemotactic protein–1 but not related chemokines. Development of a sandwich Elisa and in situ detection of producing cells," *J. Immunological Methods*, 174:249–257 (1994).

Perussia et al., "Terminal Differentiation Surface Antigens of Myelomonocytic Cells are Expressed in Human Promyelocytic Leukemia Cells (HL60) treated with Chemical Inducers," *Blood*, 58(4):836–843 (Oct., 1981).

Phan et al., "Inhibition of bleomycin–induced pulmonary fibrosis by lipopolysaccharide," *Lab. Invest.*, 50(5):587–591 (May, 1984).

Phan S.H., "Fibrotic Mechanisms in Lung Diseases," in *Immunology of Inflammation*, Chapter 4, Elsevier, pp. 121–162 (1983).

Picker et al., "Physiological and Molecular Mechanisms of Lymphocyte Homing," *Annu. Rev. Immunol.*, 10:561–591 (1992).

Power et al., "Molecular Cloning and Functional Expression of a Novel CC Chemokine Receptor cDNA from a Human Basophil Cell Line," *J. Biol. Chem*, 270(33):19495–19500 (Aug. 18, 1995).

Price et al., "Expression, purification, characterization, of recombinant murine granulocyte–macrophage colony––stimulating factor and bovine interleukin–2 from yeast," *Gene*, 55:287–293 (1987).

Raport et al., "The Orphan G–Protein–Coupled Receptor–Encoding Gene V28 is Closely Related to Genes for Chemokine Receptors and is Expressed in Lymphoid and Neural Tissues," *Gene*, 163:295–299 (1995).

Ribeiro et al., "Partial characterization of the RNA from LPS–stimulated macrophages that induces the release of chemotactic cytokines by resident macrophages," *Mol. Cell. Biochem.*, 148(2):105–113 (1995).

Rose et al., "Propagation and Expression of Cloned Genes in Yeast: 2–μm Circle–Based Vectors," *Methods in Enzymology*, 185:234–279 (1990).

Sambrook et al., *Molecular Cloning: A Laboratory Manual*, Cold Spring Harbor Laboratory, Cold Spring Harbor, New York, pp. 1.74–1.84, 1.90–1.104, 6.1–6.35, and Chapter 15 (1989).

Samson et al., "Molecular Cloning and Functional Expression of a New Human CC–Chemokine Receptor Gene," *Biochemistry*, 35:3362–3367 (1996).

Sarris et al., "Human interferon–inducible Protein 10: Expression and Purification of recombinant protein demonstrate inhibition of early human hematopoietic Progenitors," *J. Exp. Med.*, 178:1127–1132 (Sep., 1993).

Schall et al., "A Human T Cell Specific Molecules a Member of a New Gene Family," *J. Immunology*, 141(3):1018–1025 (Aug. 1, 1988).

Schnölzer et al., "In situ neutralization in Boc–chemistry solid phase peptide synthesis," *Int. J. Pep. Pro. Res.*, 40:180–193 (1992).

Springer, "Traffic Signals for Lymphocyte Recirculation and leukocyte Emigration: The Multistep Paradigm," *Cell*, 76:301–314 (Jan. 28, 1994).

Stafforni et al., "Human Macrophages Secrete Platelet–activating Factor Acetylhydrolase," *J. Biol. Chem.*, 265(17):9682–9687 (Jun. 15, 1990).

Stearns et al., "Manipulating Yeast Genome Using Plasmid Vectors," *Method in Enzymology*, 185:280–297 (1990).

Stenberg et al., "Structural Analysis of the Major Immediate Early Gene of Human Cytomegalovirus," *J. Virology*, 49(1):190–199 (Jan., 1984).

Subramani et al., "Expression of the Mouse Dihydrofolate Reductase Complementary Deoxyribonucleic Acid in Simian Virus 40 Vectors," *Mol. Cell. Biol.* 1(9):854–864 (Sep., 1981).

Szabo et al., "Chemokine Class Differences in Binding to the Duffy Antigen–Erythrocyte Chemokine Receptor," *J. Biol. Chem.*, 270(43):25348–25351 (1995).

Taub et al., "Chemokines, Inflammation, and the Immune System," *Therapeutic Immunology*, 1:229–246 (1994).

Tjoelker et al., "Anti–inflammatory Properties of a Platelet Activating Factor Acetylhydrolase," *Nature*, 374:549–553 (Apr. 6, 1995).

Tuschil et al., "Interleukin–8 Stimulates Calcium Transients and Promotes Epidermal Cell Proliferation," *J. Invest. Dermatol.*, 99:294–298 (1992).

Urlaub et al., "Deletion of the Diploid Dihydrofolate Reductase Locus from Cultured Mammalian Cells," *Cell*, 33:405–412 (Jun., 1983).

Van Damme et al., "Structural and Functional Identification of Two Human, Tumor–derived Monocyte Chemotactic Proteins (MCP–2 and MCP–3) Belonging to the Chemokine Family," *J. Exp. Med.*, 176:59–65 (Jul., 1992).

von Heijne, G., "A New Method for Predicting Signal Sequence Cleavage Sites," *Nucleic Acids Res.*, 14(11):4683–4690 (1986).

Weber et al., "Monocyte Chemotactic Protein MCP–2 Activates Human Basophil and Eosinophil Leukocytes Similar to MCP–3," *J. Immunology*, 154:4166–4172 (1995).

Wells et al., "Selectivity and antagonism of chemokine receptors," *J. Leukocyte Biology*, 59:53–60 (Jan., 1996).

Wilson et al., "Expression and Characterization of TCA3: A Murine Inflammatory Protein," *J. Immunology*, 145(8):2745–2750 (Oct. 15, 1990).

Yoshimura et al., "Production and Characterization of Mouse Monoclonal Antibodies Against Human Monocyte Chemoattractant Protein–1," *J. Immunol.*, 147(7):2229–2233 (Oct., 1991).

Yoshimura, T., "cDNA Cloning of Guinea Pig Monocyte Chemoattractant Protein–1 and Expression of the Recombinant Protein,"*J. Immunol.*, 150(11):5025–5032 (Jun. 1, 1993).

Frommel et al, *J Mol Eval* 21, 1985, pp. 233–257.
Bowie et al, *Science 247*, 1990, pp. 1306–1310.
The Protein Fuldiny Problem and Testing Structue Prediction ed Merg et al, 1994, Chapter 14, by Ng et al.

ALIGNMENT OF MDC TO C-C CHEMOKINES

```
              Leader      /                              Mature
Hu MDC        MARLQTALLV VLVLLAVALQ ATEA      GPYGAN MEDSVCCRDY VRYRLPLRVV   50
Hu MCP-3      M-KASAALLC LLLTAAAFSP QGLA      QPVGIN -TSTTCCYRF INKKIPKQRL   48
Hu MCP-1      M-KVSAALLC LLLIAATFIP QGLA      QPDAIN -APVTCCYNF TNRKISVQRL   48
Hu MCP-2                                      QPD-SV SIPITCCFNV INRKIPIQRL   26
Hu RANTES     M-KVSAAALA VILIATALCA PASA      SPY-SS -DTTPCCFAY IARPLPRAHI   47
Hu MIP-1β     M-KLCVTVLS LLMLVAAFCS PALS      APM-GS DPPTACCFSY T-REASSNFV   47
Hu MIP-1α     M-QVSTAALA VLLCTMALCN QF-S      ASL-AA DTPTACCFSY TSRQIPQNFI   47
Hu I-309      MQIITTALVC LLL-AGMWPE DVDS      KS--MQ VPFSRCCFSF AEQEIPLRAI   47

Hu MDC        KH-FYWTSDS CPRPGVVLLT FRDKEICADP RVPWVKMILN KLSQ               93
Hu MCP-3      ESYRRTTSSH CPREAVIFKT KLDKEICADP TQKWVQDFMK HLDKKTQTPKL        99
Hu MCP-1      ASYRRITSSK CPKEAVIFKT IVAKEICADP KQKWVQDSMD HLDKQTQTPKT        99
Hu MCP-2      ESYTRITNIQ CPKEAVIFKT KRGKEVCADP KERWVRDSMK HLDQIFQNLKP        76
Hu RANTES     KEYFY-TSGK CSNPAVVFVT RKNRQVCANP EKKWVREYIN SLEMS              91
Hu MIP-1β     VDY-YETSSL CSQPAVVFQT KRSKQVCADP SESWVQEYVY DLELN              91
Hu MIP-1α     ADYF-ETSSQ CSKPGVIFLT KRSRQVCADP SEEWVQKYVS DLELSA             92
Hu I-309      LCY-RNTSSI CSNEGLIFKL KRGKEACALD TVGWVQRHRK MLRHCPSKRK         96
```

FIG. 1

Effects of MDC on fibroblast proliferation

5,932,703

MACROPHAGE DERIVED CHEMOKINE AND CHEMOKINE ANALOGS

This application is a continuation-in-part of U.S. patent application Ser. No. 08/558,658, filed Nov. 16, 1995, which is a continuation-in-part of U.S. patent application Ser. No. 08/479,620, filed Jun. 7, 1995.

FIELD OF THE INVENTION

The present invention relates generally to chemokines and more particularly to purified and isolated polynucleotides encoding a novel human C—C chemokine, to purified and isolated chemokine protein encoded by the polynucleotides, and to materials and methods for the recombinant production of the novel chemokine protein.

BACKGROUND

Chemokines, also known as "intercrines" and "SIS cytokines", comprise a family of small secreted proteins (e.g., 70–100 amino acids and about 8–10 kiloDaltons) which attract and activate leukocytes and thereby aid in the stimulation and regulation of the immune system. The name "chemokine" is derived from chemotactic cytokine, and refers to the ability of these proteins to stimulate chemotaxis of leukocytes. Indeed, chemokines may comprise the main attractants for inflammatory cells into pathological tissues. See generally, Baggiolini et al., Advances in Immunology, 55:97–179 (1994). While leukocytes comprise a rich source of chemokines, several chemokines are expressed in a multitude of tissues. Id., Table II.

Previously identified chemokines generally exhibit 20–70% amino acid identity to each other and contain four highly-conserved cysteine residues. Based on the relative position of the first two of these cysteine residues, chemokines have been further classified into two subfamilies. In the "C-X-C" or "α" subfamily, encoded by genes localized to human chromosome 4, the first two cysteines are separated by one amino acid. In the "C—C" or "β" subfamily, encoded by genes on human chromosome 17, the first two cysteines are adjacent. X-ray crystallography and NMR studies of several chemokines have indicated that, in each family, the first and third cysteines form a first disulfide bridge, and the second and fourth cysteines form a second disulfide bridge, strongly influencing the native conformation of the proteins. In humans alone, nearly ten distinct sequences have been described for each chemokine subfamily. Chemokines of both subfamilies have characteristic leader sequences of twenty to twenty-five amino acids.

The C-X-C chemokines, which include IL-8, GROα/β/γ, platelet basic protein, Platelet Factor 4 (PF4), IP-10, and others, share approximately 25% to 60% identity when any two amino acid sequences are compared (except for the GROα/β/γ members, which are 84–88% identical with each other). Most of the C-X-C chemokines (excluding IP-10 and Platelet Factor 4) share a common E-L-R tri-peptide motif upstream of the first two cysteine residues, and are potent stimulants of neutrophils, causing rapid shape change, chemotaxis, respiratory bursts, and degranulation. These effects are mediated by seven-transmembrane-domain rhodopsin-like G protein-coupled receptors; a receptor specific for IL-8 has been cloned by Holmes et al., Science, 253:1278–80 (1991), while a similar receptor (77% identity) which recognizes IL-8, GRO and NAP2 has been cloned by Murphy and Tiffany, Science, 253:1280–83 (1991). Progressive truncation of the N-terminal amino acid sequence of certain C-X-C chemokines, including IL-8, is associated with marked increases in activity.

The C—C chemokines, which include Macrophage Inflammatory Proteins MIP-1α and MIP-1β, Monocyte chemoattractant proteins 1, 2, and 3 (MCP-1/2/3), RANTES, I-309, and others, share 25% to 70% amino acid identity with each other. All of the previously-identified C—C chemokines activate monocytes, causing calcium flux and chemotaxis. More selective effects are seen on lymphocytes, for example, T lymphocytes, which respond best to RANTES. Five seven-transmembrane-domain G protein-coupled receptors for C—C chemokines have been cloned to date, including a C—C chemokine receptor-1 (CCR1) which recognizes MIP-1α and RANTES (Neote et al., Cell, 72:415–425 (1993)), and a CCR2 receptor which recognizes MCP-1 (Charo et al., Proc. Nat. Acad. Sci., 91:2752–56 (1994)); CCR3, which recognizes eotaxin (Combadiere, J. Biol. Chem., 270:16491 (1995)); CCR4, which recognized MIP-1α, RANTES, and MCP-1 (Power et al., J. Biol. Chem., 270:19495 (1995)); and CCR5, which recognizes MIP-1α, MIP-1β, and RANTES (Samson et al., Biochemstry, 35:3362 (1996)).

The roles of a number of chemokines, particularly IL-8, have been well documented in various pathological conditions. See generally Baggiolini et al., supra, Table VII. Psoriasis, for example, has been linked to over-production of IL-8, and several studies have observed high levels of IL-8in the synovial fluid of inflamed joints of patients suffering from rheumatic diseases, osteoarthritis, and gout.

The role of C—C chemokines in pathological conditions also has been documented, albeit less comprehensively than the role of IL-8. For example, the concentration of MCP-1 is higher in the synovial fluid of patients suffering from rheumatoid arthritis than that of patients suffering from other arthritic diseases. The MCP-1 dependent influx of mononuclear phagocytes may be an important event in the development of idiopathic pulmonary fibrosis. The role of C—C chemokines in the recruitment of monocytes into atherosclerotic areas is currently of intense interest, with enhanced MCP-1 expression having been detected in macrophage-rich arterial wall areas but not in normal arterial tissue. Expression of MCP-1in malignant cells has been shown to suppress the ability of such cells to form tumors in vivo. (See U.S. Pat. No. 5,179,078, incorporated herein by reference.) A need therefore exists for the identification and characterization of additional C—C chemokines, to further elucidate the role of this important family of molecules in pathological conditions, and to develop improved treatments for such conditions utilizing chemokine-derived products.

Chemokines of the C—C subfamily have been shown to possess utility in medical imaging, e.g., for imaging sites of infection, inflammation, and other sites having C—C chemokine receptor molecules. See, e.g., Kunkel et al., U.S. Pat. No. 5,413,778, incorporated herein by reference. Such methods involve chemical attachment of a labelling agent (e.g., a radioactive isotope) to the C—C chemokine using art recognized techniques (see, e.g., U.S. Pat. Nos. 4,965,392 and 5,037,630, incorporated herein by reference), administration of the labelled chemokine to a subject in a pharmaceutically acceptable carrier, allowing the labelled chemokine to accumulate at a target site, and imaging the labelled chemokine in vivo at the target site. A need in the art exists for additional new C—C chemokines to increase the available arsenal of medical imaging tools.

The C—C chemokines RANTES, MIP-α, and MIP-1β also have been shown to be the primary mediators of the suppressive effect of human T cells on the human immunodeficiency virus (HIV), the agent responsible for causing human Acquired Immune Deficiency Syndrome (AIDS).

These chemokines show a dose-dependent ability to inhibit specific strains of HIV from infecting cultured T cell lines [Cocchi et al., *Science,* 270:1811 (1995)]. However, not all tested strains of the virus are equally susceptible to this inhibition; therefore, a need exists for additional C—C chemokines for use as inhibitors of strains of HIV.

More generally, due to the importance of chemokines as mediators of chemotaxis and inflammation, a need exists for the identification and isolation of new members of the chemokine family to facilitate modulation of inflammatory and immune responses.

For example, substances that promote inflammation may promote the healing of wounds or the speed of recovery from conditions such as pneumonia, where inflammation is important to eradication of infection. Modulation of inflammation is similarly important in pathological conditions manifested by inflammation. Crohn's disease, manifested by chronic inflammation of all layers of the bowel, pain, and diarrhea, is one such pathological condition. The failure rate of drug therapy for Crohn's disease is relatively high, and the disease is often recurrent even in patients receiving surgical intervention. The identification, isolation, and characterization of novel chemokines facilitates modulation of inflammation.

Similarly, substances that induce an immune response may promote palliation or healing of any number of pathological conditions. Due to the important role of leukocytes (e.g., neutrophils and monocytes) in cell-mediated immune responses, and due to the established role of chemokines in leukocyte chemotaxis, a need exists for the identification and isolation of new chemokines to facilitate modulation of immune responses.

Additionally, the established correlation between chemokine expression and inflammatory conditions and disease states provides diagnostic and prognostic indications for the use of chemokines, as well as for antibody substances that are specifically immunoreactive with chemokines; a need exists for the identification and isolation of new chemokines to facilitate such diagnostic and prognostic indications.

In addition to their ability to attract and activate leukocytes, some chemokines, such as IL-8, have been shown to be capable of affecting the proliferation of non-leukocytic cells. See Tuschil, *J. Invest. Dermatol.,* 99:294–298 (1992). A need exists for the identification and isolation of new chemokines to facilitate modulation of such cell proliferation.

For all of the aforementioned reasons, a need exists for recombinant methods of production of newly discovered chemokines, which methods facilitate clinical applications involving the chemokines and chemokine inhibitors.

SUMMARY OF THE INVENTION

The present invention provides novel purified and isolated polynucleotides and polypeptides that fulfill one or more of the needs outlined above.

For example, the invention provides purified and isolated polynucleotides (i.e., DNA and RNA, both sense and antisense strands) encoding a novel human chemokine of the C—C subfamily, herein designated "Macrophage Derived Chemokine" or "MDC". Preferred DNA sequences of the invention include genomic and cDNA sequences and chemically synthesized DNA sequences.

The nucleotide sequence of a cDNA, designated MDC cDNA, encoding this chemokine, is set forth in SEQ ID NO: 1, which sequence includes 5' and 3' non-coding sequences. A preferred DNA of the present invention comprises nucleotides 20 to 298 of SEQ ID NO. 1, which nucleotides comprise the MDC coding sequence.

The MDC protein comprises a putative twenty-four amino acid signal sequence at its amino terminus. A preferred DNA of the present invention comprises nucleotides 92 to 298 of SEQ ID NO. 1, which nucleotides comprise the putative coding sequence of the mature (secreted) MDC protein, without the signal sequence.

The amino acid sequence of chemokine MDC is set forth in SEQ ID NO: 2. Preferred polynucleotides of the present invention include, in addition to those polynucleotides described above, polynucleotides that encode the amino acid sequence set forth in SEQ ID NO: 2, and that differ from the polynucleotides described in the preceding paragraphs only due to the well-known degeneracy of the genetic code.

Similarly, since twenty-four amino acids (positions −24 to −1) of SEQ ID NO: 2 comprise a putative signal peptide that is cleaved to yield the mature MDC chemokine, preferred polynucleotides include those which encode amino acids 1 to 69 of SEQ ID NO: 2. Thus, a preferred polynucleotide is a purified polynucleotide encoding a polypeptide having an amino acid sequence comprising amino acids 1–69 of SEQ ID NO: 2.

Among the uses for the polynucleotides of the present invention is the use as a hybridization probe, to identify and isolate genomic DNA encoding human MDC, which gene is likely to have a three exon/two intron structure characteristic of C—C chemokines genes. (See Baggiolini et al., supra); to identify and isolate DNAs having sequences encoding non-human proteins homologous to MDC; to identify human and non-human chemokines having similarity to MDC; and to identify those cells which express MDC and the conditions under which this protein is expressed.

Hybridization probes of the invention also have diagnostic utility, e.g., for screening for inflammation in human tissue, such as colon tissue. More particularly, hybridization studies using an MDC polynucleotide hybridization probe distinguished colon tissue of patients with Crohn's disease (MDC hybridization detected in epithelium, lamina propria, Payer's patches, and smooth muscle) from normal human colon tissue (no hybridization above background).

Generally speaking, a continuous portion of the MDC cDNA of the invention that is at least about 14 nucleotides, and preferably about 18 nucleotides, is useful as a hybridization probe of the invention. Thus, in one embodiment, the invention includes a DNA comprising a continuous portion of the nucleotide sequence of SEQ ID NO: 1 or of the non-coding strand complementary thereto, the continuous portion comprising at least 18 nucleotides, the DNA being capable of hybridizing under stringent conditions to a coding or non-coding strand of a human MDC gene. For diagnostic utilities, hybridization probes of the invention preferably show hybridization specificity for MDC gene sequences. Thus, in a preferred embodiment, hybridization probe DNAs of the invention fail to hybridize under the stringent conditions to other human chemokine genes (e.g., MCP-1 genes, MCP-2 genes, MCP-3 genes, RANTES genes, MIP-1α genes, MIP-1β genes, and I-309 genes, etc.).

In another aspect, the invention provides a purified polynucleotide which hybridizes under stringent conditions to the non-coding strand of the DNA of SEQ ID NO: 1. Similarly, the invention provides a purified polynucleotide which, but for the redundancy of the genetic code, would hybridize under stringent conditions to the non-coding strand of the DNA of SEQ ID NO: 1. Exemplary stringent hybridization conditions are as follows: hybridization at 42° C. in 5× SSC, 20 mM NaPO₄, pH 6.8, 50% formamide; and washing at 42° C. in 0.2× SSC. Those skilled in the art understand that it is desirable to vary these conditions empirically based on the length and the GC nucleotide base content of the sequences to by hybridized, and that formulas for determining such variation exist. [See, e.g., Sambrook et al., *Molecular Cloning: a Laboratory Manual.* Second Edition, Cold Spring Harbor, N.Y.: Cold Spring Harbor Laboratory (1989).]

In another aspect, the invention includes plasmid and viral DNA vectors incorporating DNAs of the invention, including any of the DNAs described above or elsewhere herein. Preferred vectors include expression vectors in which the incorporated MDC-encoding cDNA is operatively linked to an endogenous or heterologous expression control sequence. Such expression vectors may further include polypeptide-encoding DNA sequences operably linked to the MDC-encoding DNA sequences, which vectors may be expressed to yield a fusion protein comprising the MDC polypeptide of interest.

In another aspect, the invention includes a prokaryotic or eukaryotic host cell stably transfected or transformed with a DNA or vector of the present invention. In preferred host cells, the mature MDC polypeptide encoded by the DNA or vector of the invention is expressed. The DNAs, vectors, and host cells of the present invention are useful, e.g., in methods for the recombinant production of large quantities of MDC polypeptides of the present invention. Such methods are themselves aspects of the invention. For example, the invention includes a method for producing MDC wherein a host cell of the invention is grown in a suitable nutrient medium and MDC protein is isolated from the cell or the medium.

In yet another aspect, the invention includes purified and isolated MDC polypeptides. A preferred peptide is a purified chemokine polypeptide having an amino acid sequence comprising amino acids 1 to 69 of SEQ ID NO: 2. The polypeptides of the present invention may be purified from natural sources, but are preferably produced by recombinant procedures, using the DNAs, vectors, and/or host cells of the present invention, or are chemically synthesized. Purified polypeptides of the invention may be glycosylated or non-glycosylated, water soluble or insoluble, oxidized, reduced, etc., depending on the host cell selected, recombinant production method, isolation method, processing, storage buffer, and the like.

Moreover, an aspect of the invention includes MDC polypeptide analogs wherein one or more amino acid residues is added, deleted, or replaced from the MDC polypeptides of the present invention, which analogs retain one or more of the biological activities characteristic of the C—C chemokines. The small size of MDC facilitates chemical synthesis of such polypeptide analogs, which may be screened for MDC biological activities (e.g., the ability to induce macrophage chemotaxis, or inhibit monocyte chemotaxis) using the many activity assays described herein. Alternatively, such polypeptide analogs may be produced recombinantly using well-known procedures, such as site-directed mutagenesis of MDC-encoding DNAs of the invention.

In a related aspect, the invention includes polypeptide analogs wherein one or more amino acid residues is added, deleted, or replaced from the MDC polypeptides of the present invention, which analogs lack the biological activities of C—C chemokines or MDC, but which are capable of competitively or non-competitively inhibiting the binding of MDC polypeptides with a C—C chemokine receptor. Such polypeptides are useful, e.g., for modulating the biological activity of endogenous MDC in a host, as well as useful for medical imaging methods described above.

Certain specific analogs of MDC are contemplated to modulate the structure, intermolecular binding characteristics, and biological activities of MDC. For example, amino-terminal (N-terminal) and carboxy-terminal (C-terminal) deletion analogs (truncations) are specifically contemplated to change MDC structure and function.

Additionally, the following single-amino acid alterations (alone or in combination) are specifically contemplated: (1) substitution of a non-basic amino acid for the basic arginine and/or lysine amino acids at positions 24 and 27, respectively, of SEQ ID NO: 2; (2) substitution of a charged or polar amino acid (e.g., serine, lysine, arginine, histidine, aspartate, glutamate, asparagine, glutamine or cysteine) for the tyrosine amino acid at position 30 of SEQ ID NO: 2, the tryptophan amino acid at position 59 of SEQ ID NO: 2, and/or the valine amino acid at position 60 of SEQ ID NO: 2; and (3) substitution of a basic or small, non-charged amino acid (e.g., lysine, arginine, histidine, glycine, alanine) for the glutamic acid amino acid at position 50 of SEQ ID NO: 2. Specific analogs having these amino acid alterations are encompassed by the following formula (SEQ ID NO: 25):

```
Met Ala Arg Leu Gln Thr Ala Leu Leu Val Val Leu Val Leu Leu Ala
-24             -20                 -15                 -10

Val Ala Leu Gln Ala Thr Glu Ala Gly Pro Tyr Gly Ala Asn Met Glu
            -5                      1                5

Asp Ser Val Cys Cys Arg Asp Tyr Val Arg Tyr Arg Leu Pro Leu Xaa
        10              15              20

Val Val Xaa His Phe Xaa Trp Thr Ser Asp Ser Cys Pro Arg Pro Gly
25              30              35                      40

Val Val Leu Leu Thr Phe Arg Asp Lys Xaa Ile Cys Ala Asp Pro Arg
            45              50                      55

Val Pro Xaa Xaa Lys Met Ile Leu Asn Lys Leu Ser Gln
            60              65
``` wherein the amino acid at position 24 is selected from the group consisting of arginine, glycine, alanine, valine, leucine, isoleucine, proline, serine, threonine, phenylalanine, tyrosine, tryptophan, aspartate, glutamate, asparagine, glutamine, cysteine, and methionine; wherein the amino acid at position 27 is independently selected from the group consisting of lysine, glycine, alanine, valine, leucine, isoleucine, proline, serine, threonine, phenylalanine, tyrosine, tryptophan, aspartate, glutamate, asparagine, glutamine, cysteine, and methionine; wherein the amino acid at position 30 is independently selected from the group consisting of tyrosine, serine, lysine, arginine, histidine, aspartate, glutamate, asparagine, glutamine, and cysteine; wherein the amino acid at position 50 is independently selected from the group consisting of glutamic acid, lysine, arginine, histidine, glycine, and alanine; wherein the amino acid at position 59 is independently selected from the group consisting of tryptophan, serine, lysine, arginine, histidine, aspartate, glutamate, asparagine, glutamine, and cysteine; and wherein the amino acid at position 60 is independently selected from the group consisting of valine, serine, lysine, arginine, histidine, aspartate, glutamate, asparagine, glutamine, and cysteine. Such MDC polypeptide analogs are specifically contemplated to modulate the binding characteristics of MDC to chemokine receptors and/or other molecules (e.g., heparin, glycosaminoglycans, erythrocyte chemokine receptors) that are considered to be important in presenting MDC to its receptor. In one preferred embodiment, MDC polypeptide analogs of the invention comprise amino acids 1 to 69 of SEQ ID NO: 25.

The following additional analogs have been synthesized and also are intended as aspects of the invention: (a) a polypeptide comprising a sequence of amino acids identified by positions 1 to 70 of SEQ ID NO: 30; (b) a polypeptide comprising a sequence of amino acids identified by positions 9 to 69 of SEQ ID NO: 2; (c) a polypeptide comprising a sequence of amino acids identified by positions 1 to 69 of SEQ ID NO: 31; and (d) a polypeptide comprising a sequence of amino acids identified by positions 1 to 69 of SEQ ID NO: 32.

In related aspects, the invention provides purified and isolated polynucleotides encoding such MDC polypeptide analogs, which polynucleotides are useful for, e.g., recombinantly producing the MDC polypeptide analogs; plasmid and viral vectors incorporating such polynucleotides, and prokaryotic and eukaryotic host cells stably transformed with such DNAs or vectors.

In another aspect, the invention includes antibody substances (e.g., monoclonal and polyclonal antibodies, single chain antibodies, chimeric or humanized antibodies, and the like) which are immunoreactive with MDC polypeptides and polypeptide analogs of the invention. Such antibodies are useful, e.g., for purifying polypeptides of the present invention, for quantitative measurement of endogenous MDC in a host, e.g., using well-known ELISA techniques, and for modulating binding of MDC to its receptor(s). The invention further includes hybridoma cell lines that produce antibody substances of the invention.

Recombinant MDC polypeptides and polypeptide analogs of the invention may be utilized in a like manner to antibodies in binding reactions, to identify cells expressing receptor(s) of MDC and in standard expression cloning techniques to isolate polynucleotides encoding the receptor (s). Such MDC polypeptides, MDC polypeptide analogs, and MDC receptor polypeptides are useful for modulation of MDC chemokine activity, and for identification of polypeptide and chemical (e.g., small molecule) MDC agonists and antagonists.

Additional aspects of the invention relate to pharmaceutical utilities of MDC polypeptides and polypeptide analogs of the invention. For example, MDC has been shown to modulate leukocyte chemotaxis. In particular, MDC has been shown to induce macrophage chemotaxis and to inhibit monocyte chemotaxis. Thus, in one aspect, the invention includes a method for modulating (e.g., up-regulating or down-regulating) leukocyte chemotaxis in a mammalian host comprising the step of administering to the mammalian host an MDC polypeptide or polypeptide analog of the invention, wherein the MDC polypeptide or MDC polypeptide analog modulates leukocyte chemotaxis in the host. In preferred methods, the leukocytes are monocytes and/or macrophages. For example, empirically determined quantities of MDC are administered (e.g., in a pharmaceutically acceptable carrier) to induce macrophage chemotaxis or to inhibit monocyte chemotaxis, whereas inhibitory MDC polypeptide analogs are employed to achieve the opposite effect.

In another aspect, the invention provides a method for palliating an inflammatory condition in a patient, the condition characterized by at least one of (i) monocyte chemotaxis toward a site of inflammation in said patient or (ii) fibroblast cell proliferation, the method comprising the step of administering to the patient a therapeutically effective amount of MDC. In one embodiment, a therapeutically effective amount of MDC is an amount capable of inhibiting monocyte chemotaxis. In another embodiment, a therapeutically effective amount of MDC is an amount capable of inhibiting fibroblast cell proliferation. Such therapeutically effective amounts are empirically determined using art-recognized dose-response assays.

As an additional aspect, the invention provides a pharmaceutical composition comprising an MDC polypeptide or polypeptide analog of the invention in a pharmaceutically acceptable carrier. Similarly, the invention relates to the use of a composition according to the invention for the treatment of disease states, e.g., inflammatory disease states. In one embodiment, the inflammatory disease state is characterized by monocyte chemotaxis toward a site of inflammation in a patient having the disease state. In another embodiment, the inflammatory disease state is characterized by fibroblast cell proliferation in a patient having the disease state.

The foregoing aspects and numerous additional aspects will be apparent from the drawing and detailed description which follow.

BRIEF DESCRIPTION OF THE DRAWING

FIG. 1 is a comparison of the amino acid sequence of human MDC (SEQ ID NO: 2) with the amino acid sequences of other, previously characterized human C—C chemokines: MCP-3 [Van Damme et al., *J. Exp. Med.,* 176:59 (1992)] (SEQ ID NO: 18); MCP-1 [Matsushima et al., *J. Exp. Med.,* 169:1485 (1989)] (SEQ ID NO: 19); MCP-2 (mature form) [Van Damme et al., supra; Chang et al., *Int. Immunol.,* 1:388 (1989)] (SEQ ID NO: 20); RANTES [Schall et al., *J. Immunol.,* 141:1018 (1988)] (SEQ ID NO: 21); MIP-1β [Brown et al., *J. Immunol.,* 142:679 (1989)] (SEQ ID NO: 22); MIP-1α [Nakao et al., *Mol. Cell Biol.,* 10:3646 (1990)] (SEQ ID NO: 23); and I-309 [Miller et al., *J. Immunol.,* 143:2907 (1989)] (SEQ ID NO: 24). A slash "/" marks the site at which putative signal peptides are cleaved. Dashes are inserted to optimize alignment of the sequences.

DETAILED DESCRIPTION

Figure 2:
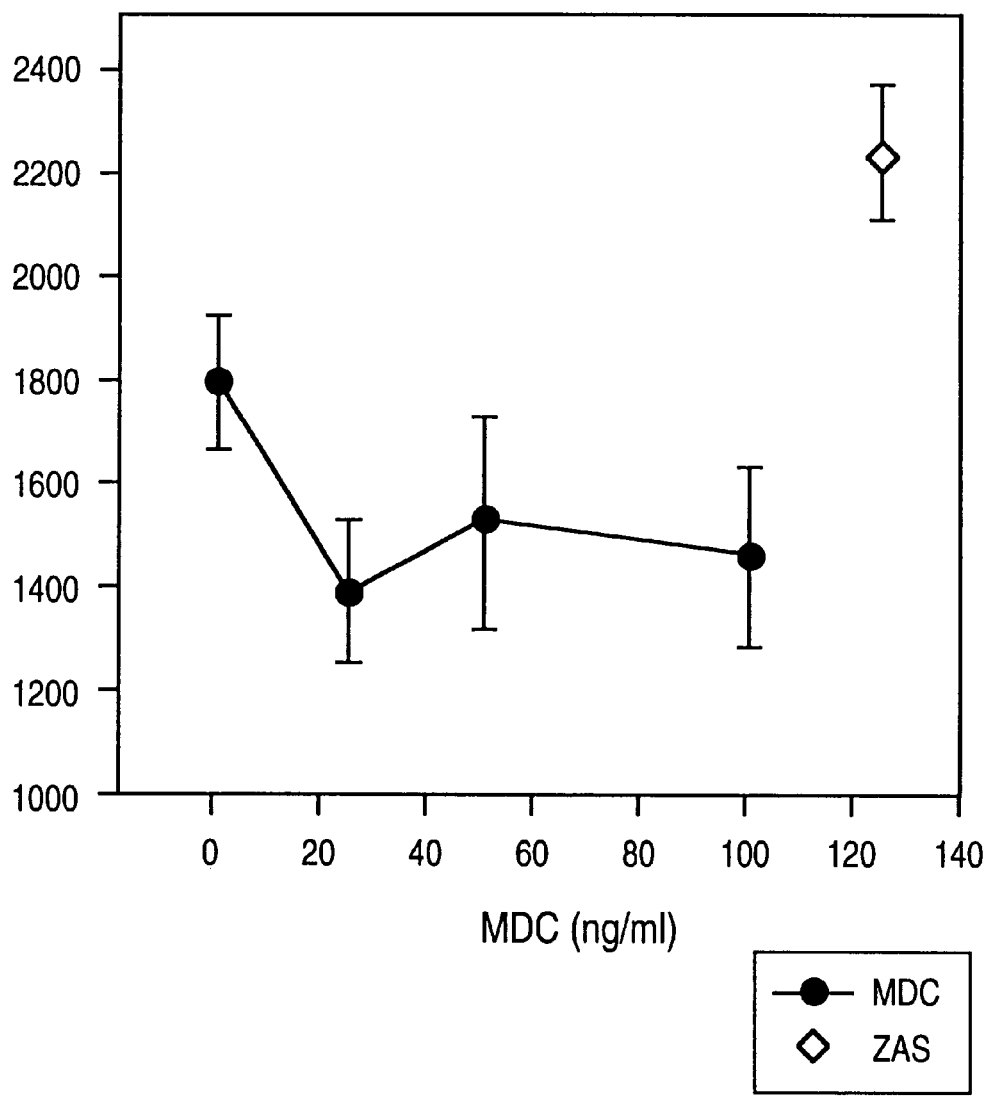
FIG. 2 is a graph depicting the chemotactic effect (measured in fluorescence units) of increasing concentrations of MDC on human mononuclear cell migration in a chemotaxis assay. Closed circles show the response of human mononuclear cells derived from the cell line THP-1. The open diamond shows the response to the positive control, zymosan activated serum (ZAS).

The present invention is illustrated by the following examples related to a human cDNA, designated MDC cDNA, encoding a novel C—C chemokine designated MDC (for "macrophage-derived chemokine"). More particularly, Example 1 describes the isolation of a partial MDC cDNA from a human macrophage cDNA library. Example 2 describes the isolation of additional cDNAs from the cDNA library using the cDNA from Example 1 as a probe, one of these additional cDNAs containing the entire MDC coding sequence. Additionally, Example 2 presents a composite MDC cDNA nucleotide sequence and presents a characterization of the deduced amino acid sequence of the chemokine (MDC) encoded thereby. In Example 3, experiments are described which reveal the level of MDC gene expression in various human tissues. The greatest MDC gene expression was observed in the thymus, with much weaker expression detectable in spleen and lung tissues. Example 4 describes more particularly the expression of the MDC gene during monocyte maturation into macrophages and during inducement of HL60 cell differentiation to a macrophage-like cell type.

Since MDC gene expression was detected in thymus and spleen in Example 3, in situ hybridization studies were conducted to localize further the MDC gene expression in these tissues. Moreover, in situ hybridization revealed a correlation between elevated MDC gene expression in intestinal tissue and Crohn's disease. These in situ hybridization experiments are described in Example 5.

Example 6 describes the recombinant production of MDC as a GST fusion protein in prokaryotic cells, as well as the cleavage of the fusion protein and purification of the recombinant MDC. Example 7 describes the construction of an alternative DNA construct useful for expression of recombinant MDC protein, and describes the production of MDC by a bacterial host transformed with this construct.

Example 8 provides experimental protocols for purification of the recombinant MDC produced as described in Example 7. Examples 9 and 10 provide experimental protocols for the recombinant production of MDC in yeast and mammalian cells, respectively. In addition, Example 10 provides protocols for purification of recombinant MDC. Example 11 describes production of MDC and MDC polypeptide analogs by peptide synthesis.

Examples 12–17 provide protocols for the determination of MDC biological activities. For instance, Example 12 provides an assay of MDC effects upon basophils, mast cells, and eosinophils. Example 13 describes assays of chemoattractant and cell-activation properties of MDC on monocytes/macrophages, neutrophils, and granulocytes.

Examples 14–17 provide protocols for the determination of MDC biological activities in vivo. Example 14 provides an MDC tumor growth-inhibition assay. Examples 15 and 16 provide protocols for assaying MDC activity via intraperitoneal and subcutaneous injection, respectively. Example 17 provides protocols for determining the myelosuppressive activity of MDC.

Example 18 provides a protocol for generating monoclonal antibodies that are specifically immunoreactive with MDC.

The remaining examples provide additional MDC activity assays. For example, Example 19 provides a calcium flux assay for determining the ability of MDC to induce cellular activation. Example 20 provides an assay for determining the HIV anti-proliferative effects of MDC. Example 21 demonstrates the anti-proliferative effects of MDC on fibroblasts. Example 22 provides in vitro assays for the effects of MDC upon the proliferation of additional cell types. Example 23 provides an in vivo assay for determining the anti-proliferative effects of MDC on fibroblasts. Example 24 provides assays for identifying MDC modulators.

EXAMPLE 1

Isolation of a Partial C—C chemokine cDNA

A partial cDNA for a new C—C chemokine was isolated as follows. Poly A$^+$ RNA was harvested from peripheral blood monocyte-derived macrophages. Double-stranded, blunt-ended cDNA was generated using the Invitrogen Copy Kit (San Diego, Calif.) and BstXI adapters were ligated to the CDNA prior to insertion into the mammalian expression vector, pRc/CMV (Invitrogen) [See, Tjoelker et al., *Nature*, 374:549–552 (1995)]. *E. coli* XL1-Blue bacteria (Stratagene, La Jolla, Calif.) were transformed via electroporation with the plasmid cDNA library and plated onto 986 plates containing 100 μg/ml carbenicillin (approximately 3000 transformants per plate). After overnight growth at 37° C., the bacteria were scraped off of each plate to form 986 bacterial pools. Plasmid DNA was isolated from each of the 986 bacterial pools using the Magic Miniprep DNA Purification System (Promega, Madison, Wis.) according to the manufacturer's directions.

The purified plasmid DNA pools were used to isolate individual cDNA clones for further characterization, as follows: Plasmid DNA from individual pools was used to transform E. coli XL1-Blue cells, which were plated and grown overnight as described above. Individual transformants were randomly selected and grown overnight in 3 ml of LB media supplemented with carbenicillin for plasmid purification using the Wizard Miniprep Purification system (Promega) with the following alteration: 250 mg of diatomaceous earth (Sigma Chem. Co., St. Louis, Mo.) was added to the DNA binding resin provided by the manufacturer. Purified plasmid DNA was sequenced on a Model 373 automated sequencer (Applied Biosystems, Foster City, Calif.) using primer JHSP6:

5' GACACTATAGAATAGGGC 3' (SEQ ID NO: 3).

This primer hybridizes to plasmid vector pRc/CMV adjacent to the cloning site.

The nucleotide and deduced amino acid sequences of individual cDNAs were compared to nucleotide and peptide sequence databases to determine which of the clones encoded proteins with similarity to known inflammatory mediators. Sequence comparisons were performed on Dec. 14, 1994, by the BLAST Network Service of the National Center for Biotechnology Information (e-mail: "blast@ncbi.nlm.nih.gov"), using the alignment algorithm of Altschul et al., *J. Mol. Biol.*, 215: 403–410 (1990). The sequence analysis revealed that a portion of one of the isolated macrophage cDNA clones, designated pMP390, contained a gene sequence having approximately 60–70% identity with previously-identified chemokine genes, including the human MCP-3 gene and rat MIP-1β gene.

The 2.85 kb cDNA insert of pMP390 was subcloned into the vector pBluescript SK⁻ (Stratagene, La Jolla Calif.) to facilitate complete sequencing. Nested deletions beginning from the poly-A tail were created by digestion, using Promega's Erase-a-Base System (Madison Wis.). The deletion plasmids were recircularized, cloned in *E. coli*, purified, and sequenced using the M13, T3.1, and T7.1 primers depicted below:

(SEQ ID NO: 4) M13: 5' GTAAAACGACGGCCAGT 3'

(SEQ ID NO: 5) T3.1: 5' AATTAACCCTCAC-TAAAGGG 3'

(SEQ ID NO: 6) T7.1: 5' GTAATACGACTCACTAT-AGGGC 3'

The complete sequence of this pMP390 cDNA corresponds to nucleotides 73 to 2923 of SEQ ID NO: 1 (and to deduced amino acids -6 to 69 of SEQ ID NO 2). The sequence that was originally compared to database sequences corresponds to nucleotides 73 to 610 of SEQ ID NO: 1.

EXAMPLE 2

Isolation of additional cDNA clones having the complete MDC coding sequence

Using the pMP390 cDNA clone isolated in Example 1, additional cDNA clones were isolated from the same human macrophage cDNA library, these additional cDNAs containing additional 5' sequence and encoding the complete amino acid sequence of a macrophage derived chemokine.

First, forty of the 986 plasmid DNA pools derived from the macrophage cDNA library (Example 1) were screened by PCR to identify pools containing additional cDNA clones of interest. From the pMP390 cDNA sequence obtained in Example 1, synthetic oligonucleotide PCR primers 390-1F (deposited as SEQ ID NO: 7) and 390-2R (SEQ ID NO: 8) were constructed to amplify a 211 base pair sequence of the chemokine gene partially encoded by pMP390:

390-1F: 5' TCTATCTAGAGGCCCCTACGGCGCCAA-CATGGAAG 3'

390-2R: 5' CACCGGATCCTCATTGGCTCAGCTAT-TGAGAA 3'

Primer 390-1F corresponds to nucleotides 91–116 of SEQ ID NO: 1, preceded by the recognition site for the restriction endonucleose Xba I and 4 additional bases to facilitate cleavage by the enzyme; primer 390-2R is complementary to nucleotides 301–279 of SEQ ID NO: 1, fused to the recognition site for the enzyme BamH I, which is flanked by 4 additional bases. The Xba I and BamH I sites were added to facilitate cloning of the resultant fragment.

The 50 μl PCR reaction mixture for each selected plasmid pool contained 0.2 μg of plasmid DNA; 1.5 mM MgCl$_2$; 50 mM KCl; 10 mM Tris, pH 8.4; 0.2 mM each dNTP; 10 μg/ml each primer; and 0.5 μl Taq polymerase (5 U/μl) (Boehringer Mannheim Biochemicals (BMB), Indianapolis, Ind.). The reactions were incubated for 4 minutes at 94° C., followed by 30 cycles of denaturation for 15 seconds at 94° C., annealing for 15 seconds at 60° C., and extension for 30 seconds at 72° C.

The PCR reaction products were electrophoresed through 2% agarose gels (Life Technologies, Inc., Gaithersburg, Md.) in 0.5× TBE buffer [Sambrook et al., *Molecular Cloning: a Laboratory Manual*. Second Edition, Cold Spring Harbor, N.Y.: Cold Spring Harbor Laboratory (1989)], and visualized with Ethidium Bromide. Of the forty plasmid pools screened, six produced an intense band corresponding to the expected 230 base pair PCR fragment (which includes 211 bp of chemokine gene sequence flanked by the Xba I and BamH I restriction sites) suggesting the presence of one or more plasmids containing gene sequences related to pMP390.

To isolate such related clones, aliquots from three of the six positive plasmid pools were electroporated into *E. coli* XL1-Blue cells, which were plated and grown overnight as described in Example 1. Colonies were transferred to nitrocellulose membranes and prepared for hybridization following standard protocols (Sambrook et al., supra).

A radiolabelled MDC probe for screening the filters was prepared as follows: the 2.85 kb DNA fragment containing the MDC cDNA was excised from pMP390 by restriction enzyme digestion, purified by agarose gel electrophoresis in TAE Buffer (Sambrook, et al., supra), electroeluted, extracted with phenol and chloroform, and preciptated with ethanol. The purified fragment (250 ng) was labelled using the Random Primed DNA Labelling Kit (BMB) according the manufacturer's recommendations. The labelled probe was purified by passage through a G-50 Quick Spin column (BMB).

The filters were incubated at 42° C. for 16 hours with 5×10$^7$ counts per minute (cpm) of the probe, in 40–50 ml of a solution containing 50% formamide, 5× Denhardt's solution, 5× SSC (1×SSC is 0.15M NaCl, 15 mM sodium citrate), 50 mM sodium phosphate, pH 6.5, and 0.1 mg/ml sheared salmon sperm DNA (Sigma, St. Louis Mo.). Following hybridization, the filters were washed 3 times in 0.2× SSC and 0.2% SDS at 55° C. for 30 minutes. To visualize hybridization, the washed filters were exposed overnight at −80° C. on Kodak (Rochester, N.Y.) XAR-5 autoradiographic film with Lightning Plus intensifying screens (DuPont, Del.).

PCR was used to screen 50 of the hybridizing bacterial colonies. Fifty PCR reactions containing primers 390-1F and 390-2R were set up as described above, using bacteria from the fifty colonies in place of template DNA. Initially, the reactions were denatured at 94° C. for 8 minutes. Thereafter, 35 cycles of amplification were carried out as described above. A single colony produced the expected 230 basepair product; the plasmid contained in this clone was designated pMP390-12.

Additional MDC cDNAs of interest were identified by colony hybridization using a probe specific for the 5' end of the pMP390 insert. This probe was prepared as follows: a DNA fragment containing 211 bases of the coding region of the pMP390 cDNA (nucleotides 91–298 of SEQ. ID NO: 1) and 163 bases of the adjacent 3' non-coding region was generated by PCR as described above, using 60 ng of the pMP390 cDNA clone as template and synthetic oligonucleotides 390-1F (SEQ ID NO: 7) and 390-4R (SEQ ID NO: 9) as primers.

390-4R: 5' AATGGATCCACAGCACGGAGGTGAC-CAAG 3'

Primer 390-4R contains a BamH I restriction site followed by sequence complementary to nucleotides 461 to 442 of SEQ ID NO: 1.

The PCR product was purified by electrophoresis as described above, and fifty ng of the purified fragment was labelled with the Random Primed DNA Labelling Kit (BMB) and purified by passage through a G-50 Quick Spin column (BMB). Filters were probed with this fragment as described above, and washed three times in 0.4× SSC and 0.2% SDS at 48° C. for 30 minutes. Autoradiography was carried out as described above. Five hybridizing colonies were detected, designated MP390A, MP390B, MP390C, MP390D, and MP390E.

These five colonies and a colony transformed with pMP390-12 were isolated and grown for plasmid purification, using the Wizard Miniprep DNA Purification System (Promega, Madison, Wis.) with the addition of diatomaceous earth as described in Example 1. Plasmid DNA was sequenced on an Applied Biosystems Model 373 automated sequencer, using synthetic primer 390-3R (SEQ ID NO: 10):

390-3R: 5' AGTCAAGCTTAGGGCACTCTGGGATCG-GCAC 3'.

Primer 390-3R is complementary to bases 266–246 of SEQ ID NO: 1, and contains a Hind III restriction endonuclease site and four additional base pairs at its 5' terminus. The primer was designed to anneal upstream of primer 390-2R and downstream of nucleotide 216 of SEQ ID NO: 1, the site at which an intron is predicted in the genomic DNA encoding the chemokine of the present invention [See Danoff et al., *J. Immunology*, 152:1182–1189 (1994)].

Of the six clones, clones pMP390-12 and pMP390B contained the largest additional 5' coding sequence, each extending an additional 72 nucleotides upstream of the sequence previously obtained from the cDNA clone pMP390. A composite DNA sequence, herein designated MDC cDNA, was generated by alignment of the pMP390 and pMP390-12 cDNA sequences. This 2923 base pair composite cDNA sequence, and the deduced amino acid sequence of the chemokine MDC, are set forth in SEQ ID NOs: 1 and 2, respectively.

Manual comparison of the deduced MDC amino acid sequence with sequences of known chemokines indicates that the MDC cDNA sequence encodes a novel C—C chemokine ninety-three amino acids in length, sharing 28–34% amino acid identity with other C—C chemokines (FIG. 1 and Table 1).

TABLE 1

Percent Identity Among Amino Acid Sequences of MDC and Previously Identified C—C Chemokines

|  | MDC | MCP-1 | MCP-2 | MCP-3 | RANTES | MIP-1α | MIP-1β | I-309 |
|---|---|---|---|---|---|---|---|---|
| MDC |  | 29% | 28% | 33% | 34% | 29% | 33% | 32% |
| MCP-1 | 29% |  | 62% | 72% | 34% | 38% | 34% | 33% |
| MCP-2 | 28% | 62% |  | 59% | 30% | 36% | 33% | 34% |
| MCP-3 | 33% | 72% | 59% |  | 34% | 35% | 35% | 37% |
| RANTES | 34% | 34% | 30% | 34% |  | 50% | 44% | 22% |
| MIP-1α | 29% | 38% | 36% | 35% | 50% |  | 55% | 35% |
| MIP-1β | 33% | 34% | 33% | 35% | 44% | 55% |  | 31% |
| I-309 | 32% | 33% | 34% | 37% | 22% | 35% | 31% |  |

Importantly, the four cysteine residues characteristic of the chemokines are conserved in MDC. Five additional residues also are completely conserved in the eight sequences presented in FIG. 1.

The first 24 amino acids of the 93 amino acid MDC sequence are predominantly hydrophobic and are consistent with von Heijne's rules [*Nucleic Acids Res.*, 14: 4683–90 (1986)] governing signal cleavage. These features and the polypeptide comparison in FIG. 1 collectively suggest that the MDC cDNA encodes a twenty-four amino acid signal peptide that is cleaved to produce a mature form of MDC beginning with the glycine residue at position 1 of SEQ ID NO: 2. This prediction was confirmed by direct sequencing of MDC protein produced recombinantly in mammalian cells, as described below in Example 10. The MDC composite cDNA sequence shown in SEQ ID NO: 1 extends nineteen nucleotides upstream of the predicted initiating methionine codon, and 2.6 kb downstream of the termination codon.

EXAMPLE 3

Determination of MDC Gene Expression in Human Tissues

Northern blot analyses were conducted to determine the tissues in which the MDC gene is expressed.

The radiolabelled pMP390 5' fragment described in Example 2 (which corresponds to the region of the MDC cDNA encoding the putative mature form of MDC plus 163 bases of the adjacent 3' noncoding region) was used to probe Multiple Tissue Northern blots (Clontech, Palo Alto, Calif.) containing RNA from various normal human tissues. The probe was denatured by boiling prior to use, and the hybridizations were conducted according to the manufacturer's specifications. Autoradiographs were exposed 5 days at −80° C. with 2 intensifying screens.

The greatest MDC gene expression was observed in the thymus, with much weaker expression detectable in spleen and lung tissues. Expression of MDC in tissue from the small intestine was at even lower levels, and no expression was detected in brain, colon, heart, kidney, liver, ovary, pancreas, placenta, prostate, skeletal muscle, testis, or peripheral blood leukocytes.

EXAMPLE 4

MDC Gene Expression During Macrophage Maturation

Because the cDNAs encoding MDC were isolated from a human macrophage cDNA library, MDC gene expression during differentiation of monocytes into macrophages was examined.

A

Human monocytes from a single donor were cultured on a series of tissue culture plates, and cells from one plate were harvested after 0, 2, 4 or 6 days. See generally Elstad et al., J. Immunol. 140:1618–1624; Tjoelker et al., supra. Under these conditions, the monocytes differentiated into macrophages by days 4–6 [Stafforini et al., J. Biol. Chem., 265: 9682–9687 (1990)].

A Northern blot of RNA (10 μg per lane) isolated from the cells harvested at each time point was prepared and probed, using the radiaolabelled pMP390 fragment as described above. No signal was detectable in RNA from freshly isolated monocytes, whereas a very strong signal was generated from cells that had differentiated into macrophages after six days of culture. Cells cultured for four days produced a much weaker signal, whereas the signal generated from cells cultured for two days could be seen only after prolonged exposure of the filter.

B

To confirm the expression of MDC in differentiated human macrophages, culture supernatants were analyzed by western blotting with anti-MDC monoclonal antibodies produced as described below in Example 18. Several plates of human macrophages were differentiated by growth on plastic for eight days in the presence of macrophage colony stimulating factor (0.5 ng/ml, R&D Systems, Minneapolis, Minn.).

The medium from the differentiated macrophage cell cultures was removed and replaced with similar medium or with medium containing low density lipoprotein (LDL, Sigma), oxidized LDL (oxidized by incubation in 5 μM $CuSO_4 \cdot 5H_2O$ according to the method of Malden et al., J. Biol. Chem., 266:13901 (1991)), or dexamethazone (6 nM, Sigma Chemical Co.). Following 3 days of each treatment, the culture medium was removed, brought to pH 6.8 by the addition of HCl, and passed over a Heparin-Sepharose CL-6B column (Pharmacia, Piscataway, N.J.). The column was washed with 0.2M NaCl in 20 mM Tris, pH 8, and eluted with 0.6M NaCl in 20 mM Tris, pH 8. The eluted material was fractionated on an 18% acrylamide SDS-PAGE gel (NOVEX) and electroblotted to PVDF membrane (Millipore, Bedford Mass.). The filter was blocked, washed, and reacted with monoclonal antibodies against MDC using standard techniques (Sambrook et al.). In each of the culture media analyzed, MDC protein was detected at a concentration of approximately 0.5 μg/ml, thus confirming expression of MDC in differentiated human macrophages.

Expression of MDC also was analyzed in human epithelial cell lines. The colon epithelial cell line T84 (ATCC #CCL-248) was grown in DMEM/F12 medium (GIBCO, Gaithersburg Md.), and the lung epithelial cell line A549 (ATCC #CCL-185) was grown in F12 medium. Screening for the presence of MDC mRNA in the cells and MDC protein in the culture medium was performed as described above for macrophages. No evidence of MDC expression was detectable by either method in these cell lines.

In addition, samples of the T84 cell line were treated for 1 day with TNFα (5 ng/ml, PeproTech, Rocky Hill, N.J.), TGF-β (1 ng/ml, R&D Systems), or interferon-γ (200 U/ml, PeproTech), each with or without addition of recombinant MDC at 100 ng/ml (derived from CHO cell transfectants; see Ex. 10). Samples of the A549 cell line were treated with 50 ng/ml PMA (Sigma Chemical Co.) for 0, 1, 3, 5, or 7 days. None of these treatments resulted in detectable expression of MDC mRNA in the T84 or A549 cells when screened by Northern blotting as described above.

C

Further examination of MDC gene expression in macrophages was conducted by treating the human cell line HL60 with either 1% DMSO (Sigma Chemical Co.) or 50 ng/ml PMA (Sigma). Treatment with DMSO induces differentiation of HL60 cells into a granulocytic cell type, whereas PMA induces their differentiation into a macrophage lineage [Perussia et al., Blood, 58: 836–843 (1981)]. RNA was isolated from untreated cells and from cells treated for one or three days with DMSO or PMA, electrophoresed (10 μg/lane), and blotted. The Northern blot of the RNA was probed with the radiolabelled pMP390 5' fragment described in Example 3.

After three days of PMA treatment, the HL-60 cells clearly expressed MDC mRNA, although the level of expression was apparently less than that of macrophages after six days of culture (see above). No expression was seen after one day of treatment or in untreated cells. Further, no detectable expression of MDC was induced by treatment with DMSO for one or three days.

EXAMPLE 5

In situ hybridization

Because MDC gene expression was detected in the thymus and spleen, in situ hybridization was carried out to localize the source of the message in these tissues. Further, in situ hybridization was used to correlate MDC gene expression to inflammation of intestinal tissue associated with Crohn's disease.

To generate radiolabelled in situ hybridization probes, a DNA fragment (nucleotides 91 to 301 of SEQ ID NO: 1) containing the MDC coding region was subcloned into the vector pBluescript SK⁻. T3 and T7 RNA polymerases (BMB) were used according to the manufacturer's directions to incorporate $^{35}$S-UTP into RNA transcripts complementary to each strand of the gene.

Normal human spleen, thymus, and colon tissue samples, as well as colon tissue samples from patients with Crohn's disease, were obtained from the National Disease Research Interchange (Philadelphia, Pa.). The tissue donors were as follows: normal thymus: nineteen year old male Caucasian, death due to motor vehicle accident, tissue removed at autopsy; normal spleen: 51 year old black male, death due to cerebral hemorrhage, tissue removed at autopsy; normal colon: black female, tissue removed during surgery: Crohn's colon #1: female, race not available, 46 years old, ulcerative colitis patient, tissue removed during surgery; Crohn's colon

2: eighteen year old male, race not available, Crohn's disease patient, tissue removed during surgery.

In addition to the foregoing analyses, inflamed tonsil tissue that had been removed from a patient during tonsillectomy was probed with a non-coding portion of the MDC cDNA corresponding to nucleotides 677 to 1042 of SEQ ID NO: 1. This portion was generated by PCR amplification of the MDC cDNA clone using the primers 390-7F (SEQ ID NO:26) and 390-8R (SEQ ID NO:27):

390-7F: 5'-TAT TGG ATC CGT TCT AGC TCC CTG TTC TCC 3'

390-8R : 5'-CCA AGA ATT CCT GCA GCC ACT TTC TGG GCT C 3'

The fragment was cloned into pBluescript SK⁻ vector for generation of RNA probes as described above.

The tissue samples described in the preceding paragraphs were prepared for in situ hybridization as follows. Tissue samples were imbedded in "OCT" compound (Miles, Inc., Elkhart, Ind.) and sectioned to a thickness of 6 microns using a cryostat 2800E (Leica). The tissue sections were adhered to slides coated with Vectabond (Vector Laboratories, Burlingame, Calif.), fixed in 4% paraformaldehyde for 20 min. at 4° C., dehydrated with ethanol, and denatured at 70° C. with 70% formamide and 2× SSC.

Hybridizations were performed by incubating the slides for 16 hours at 55° C. with the radiolabelled sense or anti-sense strand of the appropriate probe in an aqueous hybridization solution containing 50% formamide, 0.3M NaCl, 20 mM Tris pH 7.5, 10% dextran sulfate, 1X Denhardt's solution, 100 nM dithiothreitol, and 5 mM EDTA. After hybridization, the slides were incubated for one hour at room temperature in 4× SSC and 10 mM DTT. The slides were then washed at room temperature in 2× SSC; at 60° C. in 1× SSC; and finally at room temperature in 0.1× SSC. Specimens were dehydrated in ethanol and then coated with Kodak NTB2 photographic emulsion, air-dried for 2 hours, exposed for 11 days at 4° C., developed, and counterstained with hematoxylin/eosin.

Observed hybridization of the anti-sense strand (of either probe) indicated that the MDC gene was expressed in cells throughout the cortex of normal human thymus, with weak signal in the follicles. Expression of MDC in the thymus may indicate a T lymphocyte developmental role of MDC. Expression in normal human spleen was localized to cells of the red pulp, whereas little signal was detected in the white pulp. A high level of expression in inflamed tonsil was localized to the epithelial region, although inflammatory cells appeared to have infiltrated the entire tissue sample.

Colon samples from patients with Crohn's disease exhibited hybridization in cells of the epithelium, lamina propria, Payer's patches, and smooth muscle. In contrast, normal human colon showed no hybridization above background. The observed pattern of MDC expression in the colons of Crohn's disease patients closely correlates with the expression of a macrophage-specific gene, Platelet Activating Factor Acetylhydrolase (PAF-AH) [Tjoelker et al., supra]. This result, together with the data presented in Example 4, suggest that macrophages express MDC cDNA in vivo during pathogenic inflammation. Moreover, the identification of MDC in Crohn's disease colon tissue samples suggest diagnostic relevance of MDC levels (e.g., in a patient's blood, stool sample, and/or intestinal lesions) to a patient's disease state or clinical prognosis.

EXAMPLE 6

Production of recombinant MDC

To produce recombinant MDC protein, the sequence encoding the putative mature form of the protein was amplified by PCR and cloned into the vector pGEX-3X (Pharmacia, Piscataway, N.J.). The pGEX vector is designed to produce a fusion protein comprising glutathione-S-transferase (GST), encoded by the vector, and a protein encoded by a DNA fragment inserted into the vector's cloning site.

The standard PCR conditions described in Example 2 were again employed to amplify an MDC cDNA fragment using the primers 390-2R and 390-FX2 (SEQ ID NO: 11):

5'TATCGGATCCTGGTTCCGCGTGGC-CCCTACGGCGCCAACATGGAA3'

Primer 390-FX2 contains a BamH I restriction site, followed by a sequence encoding a thrombin cleavage site [Chang et al., Eur. J. Biochem., 151: 217 (1985)] followed by bases 92–115 of SEQ ID NO: 1. The thrombin cleavage site is as follows: leucine-valine-proline-arginine-glycine-proline, in which glycine and proline are the first two residues of the mature form of MDC. Treatment of the recombinant fusion protein with thrombin is expected to cleave the arginine-glycine bond of the fusion protein, releasing the mature chemokine from the GST fusion.

The PCR product was purified by agarose gel electrophoresis, digested with BamH I endonuclease, and cloned into the BamH I site of pGEX-3X. This pGEX-3X/MDC construct was transformed into E. coli XL-1 Blue cells (Stratagene, La Jolla, Calif.), and individual transformants were isolated and grown. Plasmid DNA from individual transformants was purified and partially sequenced using an automated sequencer and primer GEX5 (SEQ ID NO: 12), which hybridizes to the pGEX-3X vector near the BamHI cloning site:

GEX5: 5' GAAATCCAGCAAGTATATAGCA 3'

The sequence obtained with this primer confirmed the presence of the desired MDC insert in the proper orientation.

Induction of the GST-MDC fusion protein was achieved by growing the transformed XL-1 Blue culture at 37° C. in LB medium (supplemented with carbenicillin) to an optical density at wavelength 600 nm of 0.4, followed by further incubation for 4 hours in the presence of 0.25 to 1.0 mM Isopropyl β-D-Thiogalactopyranoside (Sigma Chemical Co., St. Louis Mo.).

The fusion protein, produced as an insoluble inclusion body in the bacteria, was purified as follows. Cells were harvested by centrifugation; washed in 0.15M NaCl, 10 mM Tris, pH 8, 1 mM EDTA; and treated with 0.1 mg/ml lysozyme (Sigma Chemical Co.) for 15 minutes at room temperature. The lysate was cleared by sonication, and cell debris was pelleted by centrifugation for 10 minutes at 12,000×g. The fusion protein-containing pellet was resuspended in 50 mM Tris, pH 8, and 10 mM EDTA, layered over 50% glycerol, and centrifuged for 30 min. at 6000×g. The pellet was resuspended in standard phosphate buffered saline solution (PBS) free of $Mg^{++}$ and $Ca^{++}$. The fusion protein, which remained insoluble, was approximately 80–90% of the protein mass and migrated in denaturing SDS-polyacrylamide gels with a relative molecular weight of 33 kD. The protein yield, as judged by Coomassie staining, was approximately 100 mg/l of E. coli culture.

The fusion protein was subjected to thrombin digestion to cleave the GST from the mature MDC protein. The digestion reaction (20–40 μg fusion protein, 20–30 units human thrombin (4000 U/ mg (Sigma) in 0.5 ml PBS) was incubated 16–48 hrs. at room temperature and loaded on a denaturing SDS-PAGE gel to fractionate the reaction products. The gel was soaked in 0.4M KCl to visualize the GST and MDC protein bands, which migrated as fragments of approximately 26 kD and 7 kD, respectively.

The identity of the 7 kD SDS-PAGE fragment was confirmed by partial amino acid sequence analysis. First, the protein was excised from the gel, electroeluted in 25 mM Tris base and 20 mM glycine, and collected onto a PVDF membrane in a ProSpin column (Applied Biosystems, Foster City, Calif.). Subjecting the sample to automated sequencing (Applied Biosystems Model 473A, Foster City, Calif.) yielded 15 residues of sequence information, which corresponded exactly to the expected N-terminus of the predicted mature form of MDC (SEQ ID NO: 2, amino acid residues 1 to 15).

EXAMPLE 7

Construction of a Bacterial MDC Expression Vector

The portion of the MDC cDNA encoding the predicted mature MDC protein was cloned into a plasmid containing the arabinose promoter and the pelB leader sequence [see Better et al., Science, 240: 1041–43 (1988)].

More particularly, an MDC cDNA was amplified by PCR as described in Example 2, using approximately 0.1 μg of pMP390-12 as template and synthetic oligonucleotide primers 390-2R and 390-Pel (SEQ ID NO: 13):

390-Pel: 5'ATTGCCATGGCCGGCCCCTACGGCGC-CAACATGGAA 3'

Primer 390-Pel contains an Nco I restriction site, followed by two cytosine residues, followed by bases 92 to 115 of SEQ ID NO: 1.

The expected PCR product of 232 bp was purified by agarose gel electrophoresis, digested with Nco I and BamH I, and cloned along with a portion of the arabinose operon and pelB leader sequence (Better et al., supra) into the vector pUC19 (New England Biolabs, Beverly, Mass.). The resultant construct, designated P2-390, encodes a fusion of the pelB leader (encoded by the vector) to the mature MDC protein. The sequence of this construct was confirmed by automated sequencing using the primers Ara1 (SEQ ID NO: 28) and Ara2 (SEQ ID NO: 29), which anneal to the vector adjacent to the cloning site.

Ara1: 5' GCG ACT CTC TAC TGT TTC TC3'

Ara2: 5'-CAC AGG AAA CAG CTA TGA CC3'

The plasmid P2-390 was transformed into the E. coli strain MC1061 using standard procedures, and an ampicillin resistant clone was selected for MDC production. The clone was grown in a 3 liter fermenter (Applikon, Foster City, Calif.) and MDC production was induced by the addition of 50% arabinose to a final concentration of 0.1%. After one day of incubation in the presence of arabinose, the cells were harvested. Western blotting revealed that MDC was present within the cells at a level of approximately 4 μg/g of cell paste and was secreted into the culture medium to a level of approximately 1 μg/ml.

EXAMPLE 8

Purification of Recombinant MDC from Bacteria and Culture Medium

Following is an experimental protocol for purification of the recombinant MDC produced as described in Example 7.

The secreted recombinant MDC protein is purified from the bacterial culture media by, e.g., adapting methods previously described for the purification of recombinantly produced RANTES chemokine [Kuna et al., J. Immunol., 149: 636–642 (1992)], MGSA chemokine [Horuk et al., J. Biol. Chem. 268: 541–46 (1993)], and IP-10 chemokine (expressed in insect cells) [Sarris et al., J. Exp. Med., 178: 1127–1132 (1993)].

EXAMPLE 9

Recombinant Production of MDC in Yeast

Following are protocols for the recombinant expression of MDC in yeast and for the purification of the recombinant MDC.

The coding region of the MDC cDNA is amplified from pMP390-12 by PCR, using as primers synthetic oligonucleotides containing the MDC cDNA sequences present in primers 390-1F and 390-2R. A DNA encoding the yeast pre-pro-alpha leader sequence is amplified from yeast genomic DNA in a PCR reaction using one primer containing bases 1–20 of the alpha mating factor gene and another primer complimentary to bases 255–235 of this gene [Kujan and Herskowitz, Cell, 30: 933–943 (1982)]. The pre-pro-alpha leader coding sequence and MDC coding sequence fragments are ligated into a plasmid containing the yeast alcohol dehydrogenase (ADH2) promoter, such that the promoter directs expression of a fusion protein consisting of the pre-pro-alpha factor fused to the mature MDC polypeptide. As taught by Rose and Broach, Meth. Enz. 185: 234–279, D. Goeddel, ed., Academic Press, Inc., San Diego, Calif. (1990), the vector further includes an ADH2 transcription terminator downstream of the cloning site, the yeast "2-micron" replication origin, the yeast leu-2d gene, the yeast REP1 and REP2 genes, the E. coli beta-lactamase gene, and an E. coli origin of replication. The beta-lactamase and leu-2d genes provide for selection in bacteria and yeast, respectively. The leu-2d gene also facilitates increased copy number of the plasmid in yeast to induce higher levels of expression. The REP1 and REP2 genes encode proteins involved in regulation of the plasmid copy number.

The DNA construct described in the preceding paragraph is transformed into yeast cells using a known method, e.g., lithium acetate treatment [Stearns et al., Meth. Enz., supra, pp. 280–297]. The ADH2 promoter is induced upon exhaustion of glucose in the growth media [Price et al., Gene, 55: 287 (1987)]. The pre-pro-alpha sequence effects secretion of the fusion protein from the cells. Concomitantly, the yeast KEX2 protein cleaves the pre-pro sequence from the mature MDC chemokine [Bitter et. al., Proc. Natl. Acad. Sci. USA, 81: 5330–5334 (1984)].

Alternatively, MDC is recombinantly expressed in yeast using a commercially available expression system, e.g., the Pichia Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol.

The secreted MDC is purified from the yeast growth medium by, e.g., the methods used to purify MDC from bacterial and mammalian cell supernatants (see Examples 8 and 10).

EXAMPLE 10

Recombinant Production of MDC in Mammalian Cells

MDC was recombinantly produced in mammalian cells according to the following procedures.

A. Synthesis of Expression Vector 390HXE

A truncated version of the MDC cDNA was synthesized by PCR as described in Example 2, using pMP390-12 as template and the synthetic oligonucleotides 390RcH and 390RcX as primers.

(SEQ ID NO: 14) 390RcH: 5'GACCAAGCTTGAGACATACAGGACAGAGCA (SEQ. ID NO: 15) 390RcX: 5'TGGATCTAGAAGTTGGCACAGGCTTCTGG

Primer 390RcH contains a Hind III restriction site followed by bases 1 to 20 of SEQ ID NO: 1; primer 390RcX contains an Xba I restriction site followed by the sequence complimentary to bases 403 to 385 of SEQ ID NO: 1.

The expected 423 bp PCR product was purified by agarose gel electrophoresis and cloned into Hind III/Xba I-digested pRc/CMV ((In Vitrogen, San Diego Calif.) a vector which allows for direct expression in mammalian cells). The resulting plasmid, designated 390HXE, contained bases 1 to 403 of SEQ ID NO: 1. The sequence of the insert was confirmed by automated sequencing using the primers DC03 (SEQ ID NO: 16) and JHSP6.

DC03: 5' CGA AAT TAA TAC GAC TCA CT 3'

Primer DC03 anneals to the pRc/CMV vector sequence adjacent to the cloning site.

B. Synthesis of Expression Vector 390HmX

Another MDC cDNA construct was generated by PCR, using pMP390-12 as template and the primers 390RcH and 390mycRX (SEQ ID NO: 17).

390mycRX: 5'TGGATCTAGATCAATTCAAGTCCTCCTCGCT GATCAGCTTCTGCTCTTGGCTCAGCTTATTGAGAAT 3'

Primer 390mycRX contains an Xba I restriction site, a sequence complementary to the sequence encoding a "myc" epitope [Fowlkes et al., BioTechniques, 13: 422–427 (1992)], and a sequence complementary to bases 298 to 278 of SEQ ID NO: 1. This reaction amplified the expected 354 bp fragment containing bases 1 to 298 of SEQ ID NO: 1 fused to a "myc" epitope at the MDC carboxyterminus. This epitope can be used to facilitate immunoprecipitation, affinity purification, and detection of the MDC-myc fusion protein by Western blotting. The fragment was cloned into pRc/CMV to generate the plasmid 390HmX. The sequence of the insert was confirmed by automated sequencing using the primer DC03.

C. Expression of MDC in 293T and NS0 Cells

Two transfection protocols were used to express the two MDC cDNA constructs described above in subparts A. and B.: transient transfection into the human embryonic kidney cell line 293T and stable transfection into the mouse myeloma cell line NS0 (ECACC 85110503).

Transient transfection of 293T cells was carried out by the calcium phosphate precipitation protocol of Chen and Okayama, BioTechniques, 6: 632–638 (1988) and Mol. Cel. Biol., 87: 2745–2752 (1987). Cells and supernatants were harvested four days after transfection. A Northern blot was prepared from 4 µg of total RNA from each cell lysate and probed with a radiolabelled MDC fragment prepared by PCR. The template for the labelling reaction was the PCR fragment previously generated by amplifying pMP390 with the primers 390-1F and 390-4R (see Example 2). Approximately 30 ng of this fragment was employed in a PCR reaction containing the following: 1.5 mM $MgCl_2$, 50 mM KC1, 10 mM Tris, pH 8.4, 0.2 mM dATP, 0.2 mM dTTP, 0.2 mM dGTP, 1 µM dCTP, 50 µCi $\alpha^{32}$P-dCTP (DuPont/New England Nuclear, Boston Mass.), 2.5 U Taq polymerase, and 10 µg/ml each of primers 390-1F and 390-2R. The reaction was denatured by heating for 4 minutes at 94° C., followed by 15 cycles of amplification as described in Example 2. The probe was purified by passage over a G-25 Quick Spin column (BMB). Conditions for hybridization were described in Example 2. Filters were subsequently washed in 0.5×SSC and 0.2% SDS at 42° C. for 30 minutes. Autoradiography was carried out at −80° C. with one intensifying screen for sixteen hours. The MDC DNA constructs were very highly expressed in the transfected cells and not detectable in the non-transfected cells.

For stable transfections, NS0 cells were grown to 80 % confluency in D-MEM (Gibco), collected by centrifugation, and washed with PBS. Twenty µg of plasmid DNA was linearized with Sca I restriction endonuclease (BMB), added to the cells, and incubated on ice for 15 minutes in a 0.4 cm gap cuvette (BioRad, Hercules Calif.). The cells were electroporated with two pulses of 3 microfarad at 1.5 kilovolts. Cells were diluted into 20 ml D-MEM, incubated at 37° C. in 5% $CO_2$ for 24 hours, and selected by plating into 96-well plates at various dilutions in D-MEM containing 800 µg/ml geneticin. Wells containing single drug-resistant colonies were expanded in selective media. Total RNA was analyzed by Northern blotting as described in the preceding paragraph. Message for MDC was seen only in transfected cell lines.

MDC is purified from mammalian culture supernatants by, e.g., adapting methods described for the purification of recombinant TCA3 chemokine [Wilson et al., J. Immunol., 145: 2745–2750 (1990], or as described below in subpart F.

D. Expression of MDC in CHO Cells

Figure 8:
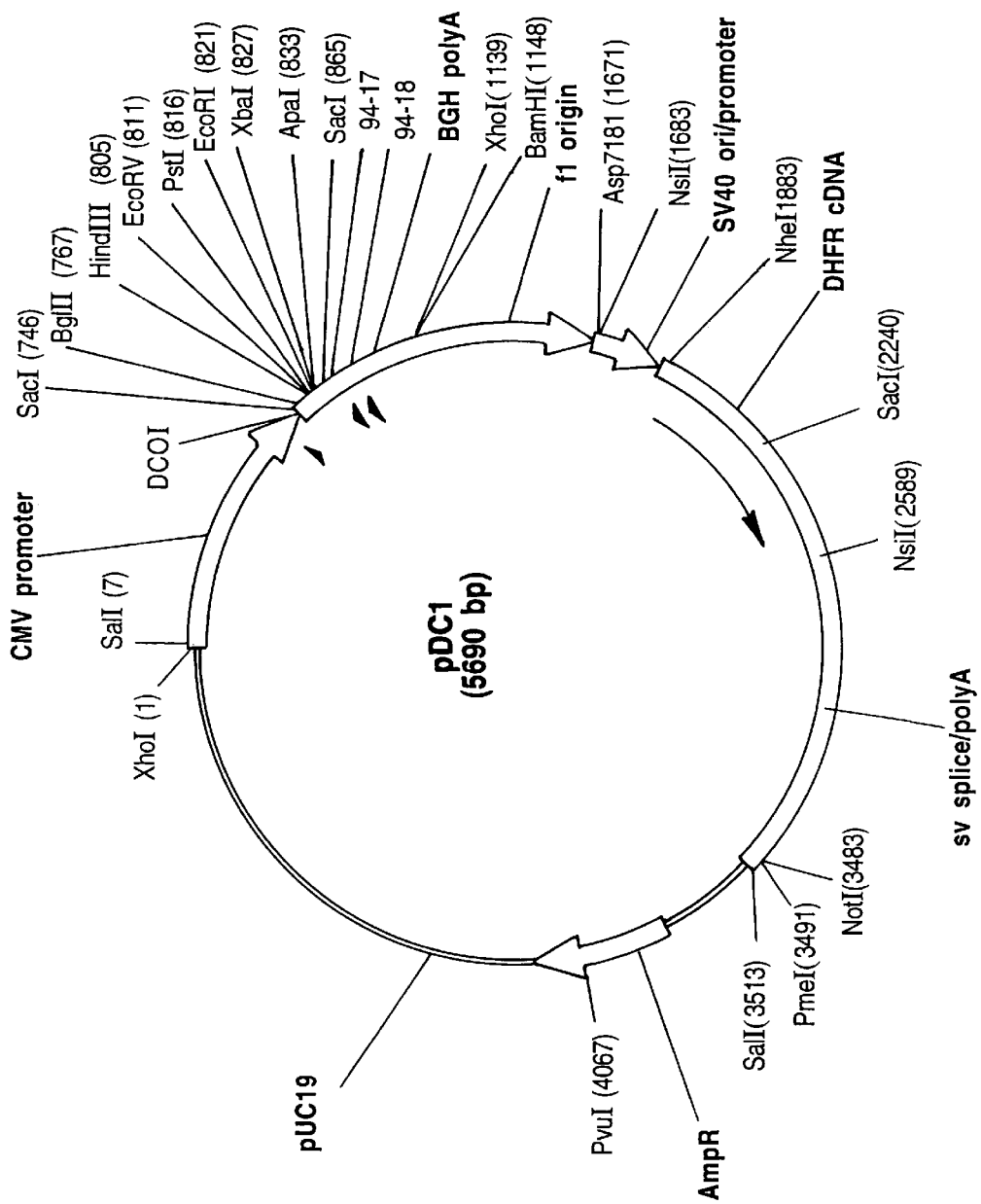
FIG. 8 schematically depicts the construction of mammalian expression vector pDC1.

PCR was used to amplify bases 1 to 403 of the MDC cDNA clone using primers 390RcH and 390RcX (SEQ. ID NOs: 14 and 15), as described above in subpart A. The fragment was cloned into the Hindil and XbaI sites of the expression vector pDC1, a pUC19 derivative that contains the cytomegalovirus (CMV) promoter to drive expression of the insert. More specifically, vector pDC1, depicted in FIG. 8, was derived from pRc/CMV and pSV2-dhfr (ATCC vector #37146). Vector pDC1 is similar to the mammalian expression vector pRc/CMV (Invitrogen, San Diego) except that pDC1 carries the mouse dihydrofolate reductase (dhfr) gene as a selectable marker, in place of the neomycin phosphotransferase gene. Transcription of the target gene in pDC1 is under the control of the strong CMV promoter. See Stenberg et al., J. Virology, 49: 190–199 (1984). Additionally, a polyadenylation sequence from the bovine growth hormone gene [Goodwin and Rottman, J. Biol. Chem., 267: 16330–16334 (1992)] is provided on the 3' side of the target gene. The dhfr expression cassette [Subramani et al., Mol. Cell. Biol. 1: 854–864 (1981)] allows selection for pDC1 in cells lacking a functional dhfr gene.

XL-1 Blue bacteria (Stratagene) were transformed with the pDC1/MDC plasmid using standard techniques of $CaCl_2$ incubation and heat shock (Sambrook et al.). Transformants were grown in LB medium containing 100 µg/ml carbenicillin. Plasmid DNA from individual transformed clones was isolated using the Promega Wizard Maxiprep system (Madison, Wis.) and its sequence was confirmed by automated sequencing using the primers 390-1F and 390-2R. The plasmid was linearized by restriction digestion with PvuI endonuclease (Boehringer Mannheim), which cuts once within the vector sequence.

The Chinese hamster ovary (CHO) cell line used for production of MDC was DG-44, which was derived by deleting the dhfr gene. See Urlaub et al., Cell, 33: 405

(1983). For electroporation, $10^7$ of these CHO cells were washed in PBS, resuspended in 1 ml PBS, mixed with 25 µg of linearized plasmid, and transferred to a 0.4 cm cuvette. The suspension was electroporated with a Biorad Gene Pulser (Richmond, Calif.) at 290 volts, 960 µFarad. Transfectants were selected by growth in $\alpha^-$ medium (Cat. No. 12000, Gibco, Gaithersburg, Md.) containing 10% dialyzed fetal bovine serum (FBS) (Hyclone, Logan, Utah) and lacking hypoxanthine and thymidine. Cells from several hundred transfected colonies were pooled and re-plated in $\alpha^-$ medium containing 20 nM methotrexate (Sigma, St. Louis, Mo.). Colonies surviving this round of selection were isolated and expanded in $\alpha^-$ medium containing 20 nM methotrexate.

E. Purification of MDC for protein sequencing

Transfected CHO clones were grown on plastic tissue culture dishes to approximately 90% confluence in $\alpha^-$ medium, at which time the medium was replaced with P5 medium containing 0.2% to 1.0% FBS. P5 medium consists of the components listed in Table 2, below (purchased as a premixed powder form Hyclone, Logan Utah), supplemented with the following additional components:

(1) 3 g/l sodium bicarbonate (Sigma, St. Louis, Mo.);

(2) 2 µg/l sodium selenite (Sigma);

(3) 1% soy bean hydrolysate (Quest International, Naarden, The Netherlands);

(4) 1×ferrous sulfate/EDTA solution (Sigma);

(5) 1.45 ml/1 EX-CYTE VLE solution (Bayer, Kankakee, Ill.);

(6) 10 µg/ml recombinant insulin (Nucellin, Eli Lily, Indianapolis, Ind.);

(7) 0.1% pluronic F-68 (Sigma);

(8) 30 µg/ml glycine (Sigma);

(9) 50 µM ethanolamine (Sigma); and

(10) 1 mM sodium pyruvate (Sigma).

TABLE 2

| Component | Powder #5 gm/L |
|---|---|
| INORGANIC SALTS | |
| Sodium Chloride | 4.0 |
| Potassium Chloride | 0.4 |
| Sodium Phosphate Dibasic, Anhydrous | 0.07102 |
| Sodium Phosphate Monobasic $H_2O$ | 0.0625 |
| Magnesium Sulfate, Anhydrous | 0.1 |
| Cupric sulfate 5 $H_2O$ | 0.00000125 |
| Ferrous Sulfate 7 $H_2O$ | 0.000417 |
| Zinc Sulfate 7 $H_2O$ | 0.0004315 |
| Ferric Nitrate 9 $H_2O$ | 0.00005 |
| Calcium Chloride, Anhydrous | 0.11661 |
| Magnesium Chloride, Anhydrous | 0 |
| AMINO ACIDS | |
| L-Alanine | 0 |
| L-Arginine HCl | 0.15 |
| L-Asparagine $H_2O$ | 0.075 |
| L-Aspartic Acid | 0.04 |
| L-Cysteine HCl $H_2O$ | 0.035 |
| L-Cystine 2 HCl | 0.12 |
| L-Glutamic Acid | 0.02 |
| L-Glutamine | 0.5846 |
| Glycine | 0.02 |
| L-Histidine HCl $H_2O$ | 0.04 |
| L-Isoleucine | 0.15 |
| L-Leucine | 0.15 |

TABLE 2-continued

| Component | Powder #5 gm/L |
|---|---|
| L-Lysine HCl | 0.1 |
| L-Methionine | 0.05 |
| L-Proline | 0.05 |
| L-Phenylainine | 0.05 |
| L-Serine | 0.075 |
| L-Threonine | 0.075 |
| L-Tryptophan | 0.02 |
| L-Tyrosine 2 Na 2 $H_2O$ | 0.075 |
| L-Valine | 0.125 |
| VITAMINS | |
| Biotin | 0.001 |
| D-Calcium Pantothenate | 0.0025 |
| Choline Chloride | 0.015 |
| Folic Acid | 0.005 |
| i-Inositol | 0.175 |
| Nicotinamide | 0.005 |
| Pyridoxal HCl | 0.005 |
| Pyrdoxine HCl | 0.005 |
| Riboflavin | 0.001 |
| Thiamine HCl | 0.005 |
| Cyanocobalamine | 0.001 |
| OTHER | |
| D-Glucose | 1.0 |
| Hypoxanthine, Na | 0.005 |
| Thymidine | 0.005 |
| Putrescine 2HCl | 0.000081 |
| Sodium Pyruvate | 0.11004 |
| Linoleic Acid | 0.0001 |
| DL-Alpha-Lipoic Acid | 0.0002 |
| Phenol Red, Na Salt | 0.0086022 |

After two additional days in culture, an aliquot of each supernatant was mixed with an equal volume of acetone. The precipitated proteins were pelleted by centrifugation, fractionated on an 18% Tris Glycine gel (NOVEX), and blotted to a PVDF membrane (Millipore, Bedford, Mass.).

MDC bound to the membrane was detected by a crude preparation of monoclonal antibody to MDC (prepared as described in Example 18). Cells from the clone secreting the highest level of MDC protein (approx. 1 µg/ml) were removed from the plate by treatment with a solution of 0.5% trypsin and 5.3 mM EDTA (GIBCO) and used to start a suspension culture in $\alpha^-$ medium plus 10% fetal bovine serum (FBS). Over the course of 8 days, 5 volumes of P5 medium were added to the culture. Proteins were precipitated from the culture supernatant by addition of polyethylene glycol (MW 8000, Union Carbide, Danbury, Conn.) to 20% (weight/volume), fractionated on an 18% Tris glycine gel, and electroblotted to a PVDF membrane (Millipore, Bedford, Mass.) in CAPS buffer (3-[Cyclohexylamino]-1-propanesulfonic acid, pH 10.4) (Sigma, St. Louis, Mo.). A strip of the filter was removed for detection of MDC by western blotting with the supernatant from a hybridoma cell line producing anti-MDC monoclonal antibodies (See Example 18). The reactive band, which migrated with an apparent molecular weight of 6.4 kD, was excised from the remaining portion of the filter.

Using an automated sequencer (Applied Biosystems, Model 473A, Foster City, Calif.), the sequence of the N-terminus of the protein was determined to be: GPYGA-NMEDS. This sequence is identical to that of residues 1 to 10 of SEQ ID NO. 2, corresponding to the N-terminus of the predicted mature form of MDC.

F. Purification of MDC for biological assays

For growth of larger cultures, MDC-expressing CHO cells were grown to 80% confluence on tissue culture plates in α⁻ medium. The cells were removed from the plates by treatment with trypsin and EDTA and resuspended at a density of 3×10⁵ cells/ml in P5 medium plus 1% FBS in a spinner flask at 37° C. Additional P5/1% FBS medium was added as needed to keep the cell density in the range of 1×10⁶ to 3×10⁶.

After 11 days in culture, the cells were removed from the medium by filtration. The pH of the culture medium was adjusted to 6.8, and it was passed over a heparin-Sepaharose CL-6B column (Pharmacia, Piscataway, N.J.). After washing with 0.2M NaCl in potassium phosphate buffer, pH 7, the column was eluted with a linear gradient of 0.2 to 0.7M NaCl. Fractions were analyzed by SDS-PAGE and Coomassie stained to determine which of them contained MDC. MDC eluted from the column at approximately 0.6M NaCl.

The fractions containing MDC were pooled and concentrated by ultrafiltration in stirred-cell chamber (Amicon, Beverly, Mass.) using a filter with a MW cutoff of 3 kD. Octylglucoside (10 mM final concentration, Boehringer Mannheim Biochemicals) was added to the concentrated MDC, which subsequently was passed through a Sephacryl HR100 column (Pharmacia, Piscataway, N.J.). Fractions were analyzed by SDS-PAGE for the presence of MDC. The final yield of MDC protein was approximately 0.1 mg/liter of culture supernatant, and the purity was estimated to be greater than 95%, as judged by Coomassie staining.

EXAMPLE 11

Production of MDC and MDC Analogs by Peptide Synthesis

MDC and MDC polypeptide analogs are prepared by chemical peptide synthesis using techniques that have been used successfully for the production of other chemokines such as IL-8 [Clark-Lewis et al., *J. Biol Chem.*, 266: 23128–34 (1991)] and MCP-1. Such methods are advantageous because they are rapid, reliable for short sequences such as chemokines, and enable the selective introduction of novel, unnatural amino acids and other chemical modifications.

For example, MDC and MDC analogs were chemically synthesized using optimized stepwise solid-phase methods [Schnolzer et al., *Int. J. Pept. Protein Res.*, 40: 180 (1992)] based on t-butyloxycarbonyl (Boc) chemistries of Merrifield [*J. Am. Chem. Soc.*, 85: 2149–2154 (1963)] on an Applied Biosystems 430A Peptide Synthesizer (Foster City, Calif.). The proteins were purified by reverse-phase HPLC and characterized by standard methods, including electrospray mass spectrometry and nuclear magnetic resonance.

The chemically synthesized MDC corresponded to the mature form of recombinant MDC, consisting of residues 1 to 69 of SEQ ID NO. 2. Several methods were used to compare the chemically synthesized MDC to the recombinant MDC produced by CHO cell transfectants as described in Example 10. The migration of chemically synthesized MDC was identical to that of the recombinant MDC in denaturing SDS-PAGE (18% Tris glycine gel, NOVEX). In addition, the proteins reacted similarly in western blot analyses using monoclonal and polyclonal antibodies raised against bacterially produced MDC as described below in Example 18. The chemically synthesized MDC also appeared to behave in the same manner as the recombinant MDC in immunoprecipitation assays with the anti-MDC monoclonal antibodies. These studies indicate that the denatured and the non-denatured structures of chemically synthesized MDC are similar to those of recombinant MDC.

The following MDC analogs also have been chemically synthesized:

1. "MDC (n+1)" (SEQ ID NO: 30) consists of Leucine followed by residues 1 to 69 of SEQ ID NO. 2.
2. "MDC (9–69)" consists of residues 9 to 69 of SEQ ID NO. 2.
3. "MDC-yl" (SEQ ID NO: 31) consists of residues 1 to 69 of SEQ ID NO. 2, with the following substitution: Residues 59–60 (Trp-Val) were replaced with the sequence Tyr-Leu.
4. "MDC-eyfy" (SEQ ID NO: 32) consists of residues 1 to 69 of SEQ ID NO. 2, with the following substitution: Residues 28–31 (His-Phe-Tyr-Trp) were replaced with the sequence Glu-Tyr-Phe-Tyr, derived from the amino acid sequence of the chemokine RANTES (residues 26–29 of SEQ ID NO: 21).

The analogs "MDC (n+1)", "MDC (9–69)", and "MDC-yl" are expected to be antagonists of MDC activity, inhibiting MDC activity by competitively binding to the same receptor that recognizes MDC. Alternatively, they may effect inhibition by forming heterodimers with the native MDC. Possible activities of the analog "MDC-eyfy" include inhibition of MDC as described for the previous analogs. In contrast, "MDC-eyfy" may behave similar to native MDC. Other activities of this analog may include functions typical of the chemokine RANTES, such as chemotaxis of T lymphocytes, monocytes, or eosinophils.

Additionally, the following single-amino acid alterations (alone or in combination) are specifically contemplated: (1) substitution of a non-basic amino acid for the basic arginine and/or lysine amino acids at positions 24 and 27, respectively, of SEQ ID NO: 2; (2) substitution of a charged or polar amino acid (e.g., serine, lysine, arginine, histidine, aspartate, glutamate, asparagine, glutamine or cysteine) for the tyrosine amino acid at position 30 of SEQ ID NO: 2, the tryptophan amino acid at position 59 of SEQ ID NO: 2, and/or the valine amino acid at position 60 of SEQ ID NO: 2; and (3) substitution of a basic or small, non-charged amino acid (e.g., iysine, arginine, histidine, glycine, alanine) for the glutamic acid amino acid at position 50 of SEQ ID NO: 2. Specific analogs having these amino acid alterations are encompassed by the following formula (SEQ ID NO: 25):

```
Met Ala Arg Leu Gln Thr Ala Leu Leu Val Val Leu Val Leu Leu Ala
-24           -20              -15              -10

Val Ala Leu Gln Ala Thr Glu Ala Gly Pro Tyr Gly Ala Asn Met Glu
         -5                    1                 5

Asp Ser Val Cys Cys Arg Asp Tyr Val Arg Tyr Arg Leu Pro Leu Xaa
        10              15              20

Val Val Xaa His Phe Xaa Trp Thr Ser Asp Ser Cys Pro Arg Pro Gly
```

```
                    25                  30                  35                  40
Val Val Leu Leu Thr Phe Arg Asp Lys Xaa Ile Cys Ala Asp Pro Arg
                        45                  50                  55
Val Pro Xaa Xaa Lys Met Ile Leu Asn Lys Leu Ser Gln
                60                  65
``` wherein the amino acid at position 24 is selected from the group consisting of arginine, glycine, alanine, valine, leucine, isoleucine, proline, serine, threonine, phenylalanine, tyrosine, tryptophan, aspartate, glutamate, asparagine, glutamine, cysteine, and methionine; wherein the amino acid at position 27 is independently selected from the group consisting of lysine, glycine, alanine, valine, leucine, isoleucine, proline, serine, threonine, phenylalanine, tyrosine, tryptophan, aspartate, glutamate, asparagine, glutamine, cysteine, and methionine; wherein the amino acid at position 30 is independently selected from the group consisting of tyrosine, serine, lysine, arginine, histidine, aspartate, glutamate, asparagine, glutamine, and cysteine; wherein the amino acid at position 50 is independently selected from the group consisting of glutamic acid, lysine, arginine, histidine, glycine, and alanine; wherein the amino acid at position 59 is independently selected from the group consisting of tryptophan, serine, lysine, arginine, histidine, aspartate, glutamate, asparagine, glutamine, and cysteine; and wherein the amino acid at position 60 is independently selected from the group consisting of valine, serine, lysine, arginine, histidine, aspartate, glutamate, asparagine, glutamine, and cysteine. Such MDC polypeptide analogs are specifically contemplated to modulate the binding characteristics of MDC to chemokine receptors and/or other molecules (e.g., heparin, glycosaminoglycans, erythrocyte chemokine receptors) that are considered to be important in presenting MDC to its receptor.

Recombinant techniques such as those described in the preceding examples also are contemplated for preparing MDC polypeptide analogs. More particularly, polynucleotides encoding MDC are modified to encode polypeptide analogs of interest using well-known techniques, e.g., site-directed mutagenesis and the polymerase chain reaction. See generally Sambrook et al., supra, Chapter 15. The modified polynucleotides are expressed recombinantly, and the recombinant MDC polypeptide analogs are purified, as described in the preceding examples.

The chemoattractant and/or cell-activation properties of MDC or MDC polypeptide analogs on one or more types of cells involved in the inflammatory process, (e.g., T lymphocytes, monocytes, macrophages, basophils, eosinophils, neutrophils, mast cells, endothelial cells, epithelial cells, fibroblasts, or others) are assayed by art-recognized techniques that have been used for numerous other chemokines. Native MDC, recombinant MDC or MDC polypeptide analogs, or synthetic MDC or MDC polypeptide analogs purified and isolated as described in one or more of the preceding examples are assayed for activity as described in the following examples with respect to MDC.

EXAMPLE 12

Assay of MDC Effects upon Basophils, Mast Cells, and Eosinophils

The effect of MDC upon basophils, mast cells, and eosinophils is assayed, e.g., by methods described by Weber et al., J. Immunol., 154: 4166–4172 (1995) for the assay of MCP-1/2/3 activities. In these methods, changes in free cytosolic calcium and release of proinflammatory mediators (such as histamine and leukotriene) are measured. Blocking chemokine-mediated activation of these cell types has implications in the treatment of late-phase allergic reactions, in which secretion of proinflammatory mediators plays a significant role [Weber et al., supra].

EXAMPLE 13

Assay of Chemoattractant and Cell-Activation Properties of MDC upon Human Monocytes/Macrophages and Human Neutrophils The effects of MDC upon human monocytes/macrophages or human neutrophils is evaluated, e.g., by methods described by Devi et al., J. Immunol., 153: 5376–5383 (1995) for evaluating murine TCA3-induced activation of neutrophils and macrophages. Indices of activation measured in such studies include increased adhesion to fibrinogen due to integrin activation, chemotaxis, induction of reactive nitrogen intermediates, respiratory burst (superoxide and hydrogen peroxide production), and exocytosis of lysozyme and elastase in the presence of cytochalasin B. As discussed by Devi et al., these activities correlate to several stages of the leukocyte response to inflammation. This leukocyte response, reviewed by Springer, Cell, 76: 301–314 (1994), involves adherence of leukocytes to endothelial cells of blood vessels, migration through the endothelial layer, chemotaxis toward a source of chemokines, and site-specific release of inflammatory mediators. The involvement of MDC at any one of these stages provides an important target for clinical intervention, for modulating the inflammatory response.

In one art-recognized chemotaxis assay, a modified Boyden chamber assay, leukocytes to be tested are fluorescently labeled with calcein by incubating for 20 minutes at room temperature. The labeled cells are washed twice with serum-free RPMI, resuspended in RPMI containing 2 mg/ml of BSA, and then added quantitatively to the upper wells of the chambers, which are separated from the lower wells by a polycarbonate filter (Neuroprobe Inc. Cabin John, MD). MDC diluted in the same medium as the leukocytes is added to the lower wells at various concentrations. Chambers are incubated for 2 hours at 37° C. At the end of the assay, cells that have not migrated through the membrane are removed by rinsing the filter with PBS and scraping with a rubber policeman. Cells that have migrated through the filter are quantitated by reading fluorescence per well in a fluorescent plate reader (Cytofluor, Millipore Inc., Boston, Mass.).

A series of experiments were performed using art-recognized procedures to determine the chemotactic properties of MDC. Initially, the response of human mononuclear cells to MDC was determined. The effect of MDC on the chemotactic response of polymorphonuclear leukocytes (granulocytes) also was examined.

It has been established that MCP-1, which is a C—C chemokine, causes both recruitment and activation of monocytes but appears to have limited ability to induce the migration of macrophages. The failure of MCP-1 to attract macrophages appears to be correlated to the differentiation process: as monocytic cells differentiate, there is a progressive decrease in cell response to MCP-1 [Denholm and Stankus, Cytokine, 7: 436–440 (1995)]. The biological activities of MCP-1 appear to correlate with the expression of this chemokine, with MCP-1 mRNA being found in monocytes but decreasing as these cells differentiate.

The pattern of expression of MDC appears to be the reverse of that described for MCP-1, with the amount of mRNA for MDC increasing as monocytes differentiate to macrophages. To determine whether this expression pattern correlates to the biological response to MDC, the effects of MDC on the migration of monocytes and macrophages were compared.

A number of different leukocyte cells types were analyzed in chemotaxis and chemotaxis inhibition assays. Human mononuclear and polymorphonuclear leukocytes were isolated from peripheral blood using methods known in the art [Denholm et al., Amer. J. Pathol., 135: 571–580 (1989)]. Second, the human monocytic cell line, THP-1 (obtained from the ATCC, Rockville, Md., and maintained in culture in RPMI with 10% FBS and with penicillin/steptomycin) was employed. THP-1 cells can be cultured as monocytes or can be induced to differentiate to macrophages by treatment with phorbol myristate acetate (PMA) [Denholm and Stankus, Cytokine, 7: 436–440 (1995)]. In some experiments monocytic THP-1 cells were employed, and in others monocytic THP-1 cells were differentiated to macrophages by incubation with phorbol myristate acetate (PMA). Third, guinea pig peritoneal macrophages were obtained essentially as described in Yoshimura, J. Immunol., 150: 5025–5032 (1993). Briefly, animals were given an intraperitoneal injection of 3% sterile thioglycollate (DIFCO) two days prior to cell harvest. Macrophages were obtained from the peritoneal cavity by lavage with phosphate buffered saline (PBS) with 1 mM EDTA and 0.1% glucose. Cells were washed once by centrifugation and then utilized in chemotaxis assays as described below.

Assays of chemotactic activity were carried out, using the cell preparations described above, essentially as described by Denholm and Stankus, Ctometry, 19: 366–369 (1995), using 96-well chambers (Neuroprobe Inc., Cabin John, Md.) and cells labeled with the fluorescent dye, calcein (Molecular Probes, Eugene, Oreg.). Polycarbonate filters used in this assay were PVP-free (Neuroprobe Inc.); filter pore sizes used for different cell types were: 5 µm for monocytes and THP-1 cells, 3 µm for polymorphonuclear leukocytes, and 8 µm for guinea pig macrophages.

Fifty thousand calcein labeled cells were resuspended in RPMI medium containing 2 mg/ml BSA and placed in the upper wells. MDC or other test substances were diluted in RPMI with BSA (e.g., fmal MDC concentrations of 25, 50, 100, 250 ng/ml) and placed in the lower wells. Following incubation at 37° C. for 2 hours, unmigrated cells remaining above the filter were removed by wiping; the filter was then air-dried. Controls in these assays were: RPMI with BSA as the negative control, and 50 ng/ml of MCP-1 and 1% zymosan activated serum (ZAS, prepared as described [Denholm and Lewis, Amer. J. Pathol., 126: 464–474, (1987)]) were used as positive controls. Migration of cells was quantitated on a fluorescent plate reader (Cytofluor, Millipore Inc. Bedford, Mass.) and the number of cells migrated expressed as fluorescent units.

In assays of inhibitory activity, cells in the upper wells of the chambers were suspended in varying concentrations (0.005, 0.05, 0.5, 5.0, and 50 ng/ml) of MDC. The lower wells of the chamber were filled with either medium alone or the chemotactic factors, MCP-1 or zymosan activated serum (ZAS). Inhibition was assessed by comparing the number of cells that migrated to MCP-1 or ZAS, in the absence of MDC, to the number of cells that migrated with increasing concentrations of MDC. Preparation of cells and quantitation of assays was performed exactly as described above for the chemotaxis assays. The number of cells migrated was expressed as fluorescent units.

As indicated in FIG. 2, MDC did not induce THP-1 - derived mononuclear cell migration, but rather appeared to inhibit mononuclear cell migration, at concentrations between 10 and 100 ng/ml. Other C—C chemokines, such as MCP-1 and RANTES, typically induce maximal monocyte chemotaxis within this concentration range.

Figure 3:
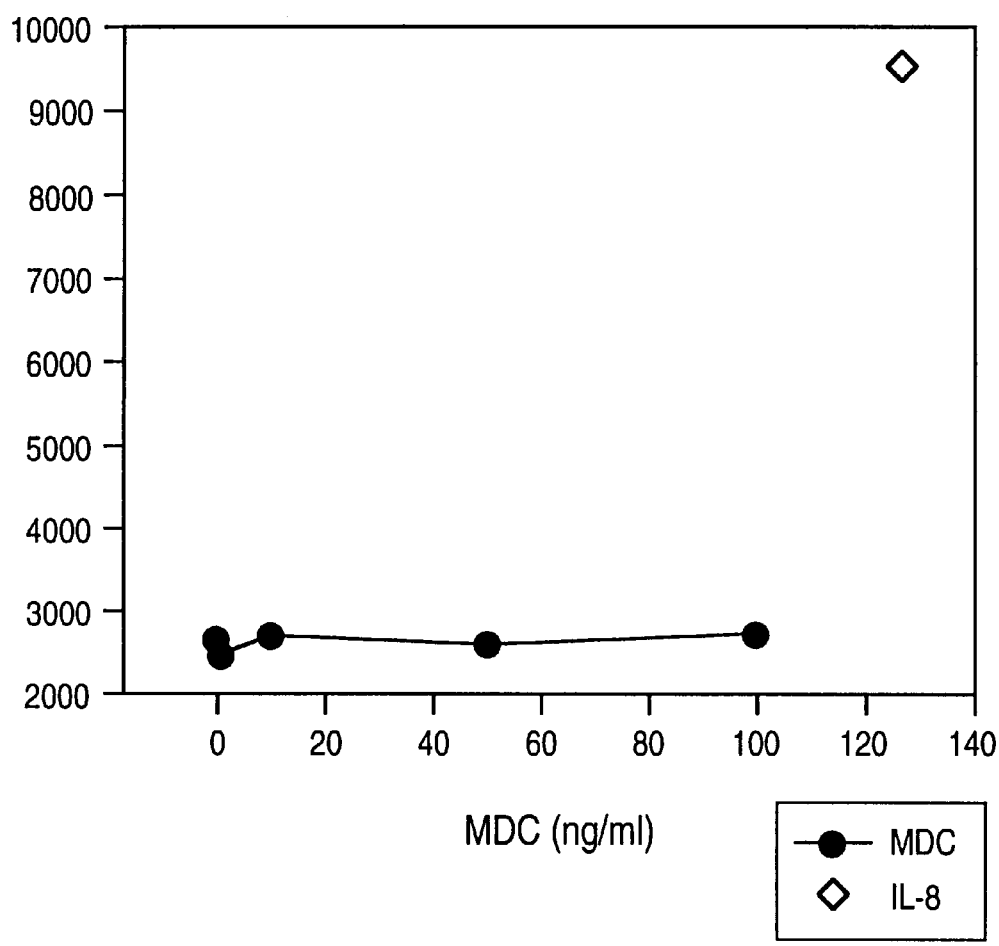
FIG. 3 is a graph depicting the chemotactic effect (measured in fluorescence units) of increasing concentrations of MDC on human polymorphonuclear (pmn) leukocyte migration. Closed circles show response to MDC, and an open diamond shows the response to the positive control, IL-8.

As shown in FIG. 3, MDC, at concentrations of 0.001 to 100 ng/ml had no net effect on granulocyte migration. In respect to this lack of effect on granulocyte chemotaxis, MDC is similar to other previously described C—C chemokines.

Figure 4:
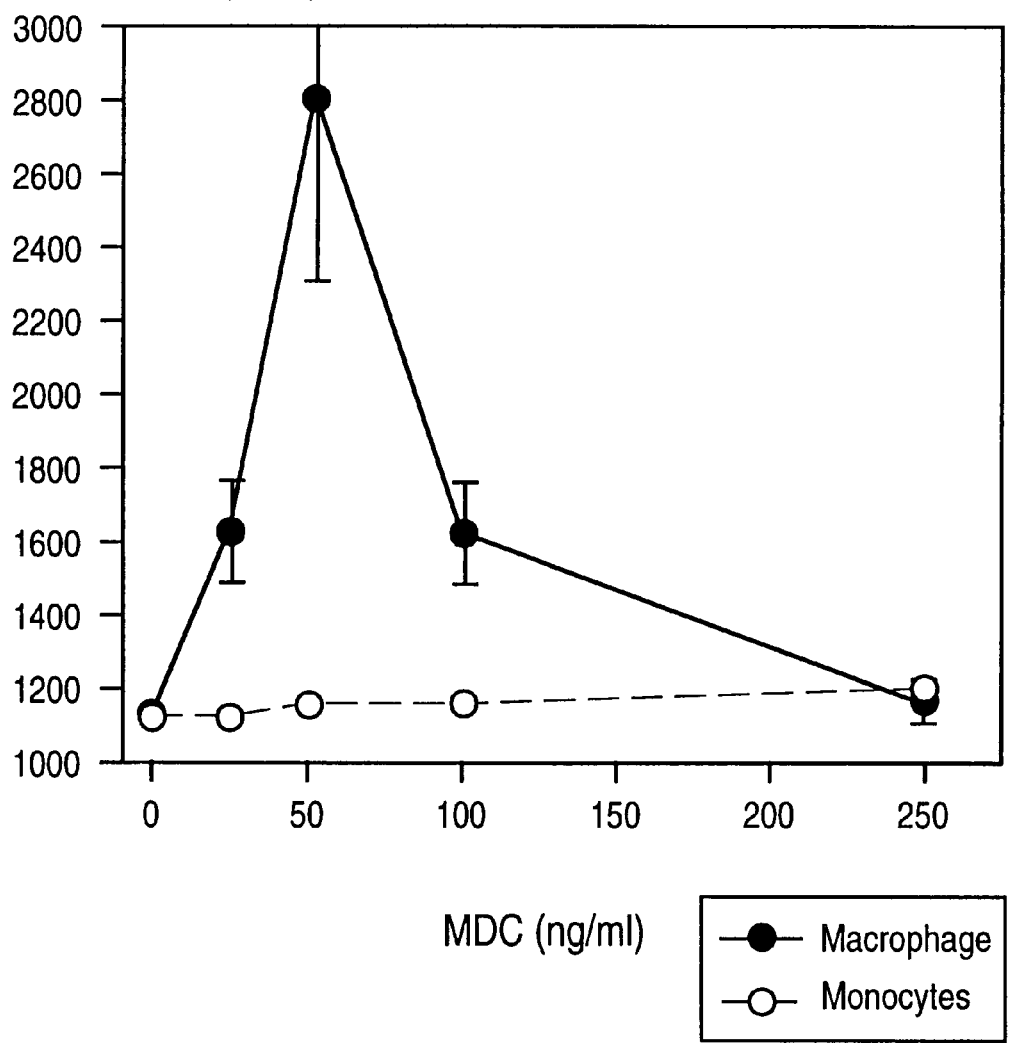
FIG. 4 is a graph depicting the chemotactic effect (measured in fluorescence units) of increasing concentrations of MDC on macrophage and monocyte migration. Closed circles show the response to MDC of macrophages derived from the cell line THP-1. Open circles show the response to MDC of monocytes derived from the cell line THP-1.

The response of both macrophage and monocyte THP-1 cells to MDC is shown in FIG. 4. Macrophages (closed circles) migrated to MDC in a dose dependent manner, with optimal activity at 50 ng/ml. The decrease in macrophage chemotactic response to MDC at higher concentrations (100 ng/ml) reflects a desensitization of cells which is typical of most chemotactic factors at high concentrations [Falk and Leonard, Infect. Immunol., 32: 464–468 (1981)]. Monocytic THP-1 cells (open circles) however, did not migrate to MDC.

Figure 5:
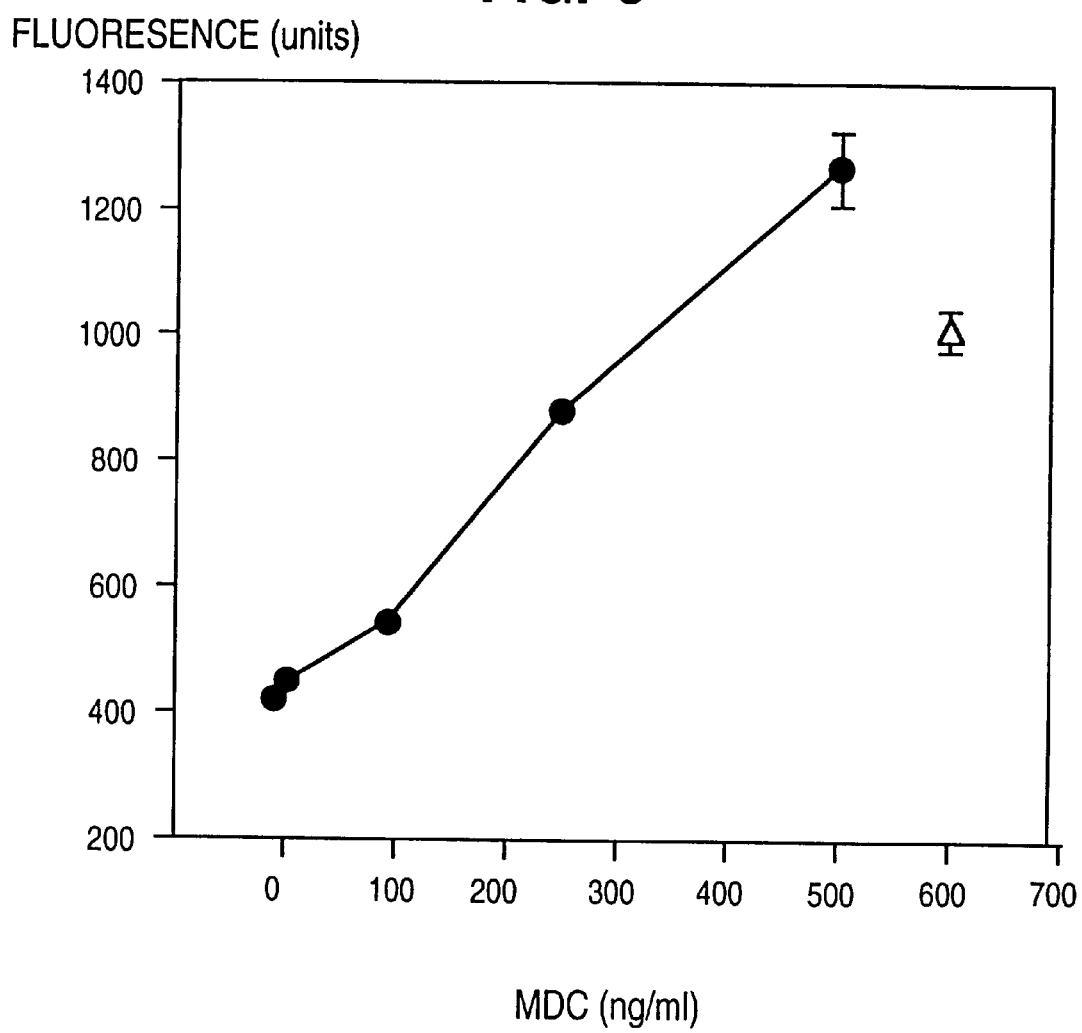
FIG. 5 is a graph depicting the chemotactic effect (measured in fluorescence units) of increasing concentrations of MDC on guinea pig peritoneal macrophage migration. Closed circles show the response of macrophages to MDC. An open triangle shows the response to the positive control, zymosan activated serum (ZAS).

The chemotactic activity of MDC for macrophages was further verified in experiments utilizing elicited guinea pig peritoneal macrophages. MDC induced a dose dependent migration of guinea pig macrophages (FIG. 5), at concentrations between 100 and 500 ng/ml. The concentrations necessary to induce the migration of guinea pig macrophages was approximately ten-fold of that for human cells (FIG. 4). Similar differences in concentrations necessary for peak biological activity of human chemokines in other species have been reported for MCP-1 by Yashimura, J. Immunol., 150: 5025–5032 (1993).

The results of these experiments suggest that the biological activities of MDC are linked to the differentiation of monocytes to macrophages. In contrast to MCP-1 [Yoshimura, J. Immunol., 150: 5025–5032 (1993)], MDC induces macrophage but not monocyte chemotaxis.

The ability of MDC to attract macrophages indicates that this chemokine might act to induce the focal accumulation of tissue macrophages. The accumulation of tissue macrophages in specific areas is important in the formation of granulomas, in which lung macrophages act to surround and enclose foreign particulates or relatively nondestructible bacterial pathogens such as Mycobacterium sp. [Adams, Am.J. Pathol., 84: 164–191 (1976)].

In certain conditions such as arthritis, the accumulation of macrophages is understood to be detrimental and destructive. The ability of MDC to promote macrophage chemotaxis indicates a therapeutic utility for MDC inhibitors of the invention, to prevent, reduce, or eliminate macrophage accumulation in tissues.

Figure 6:
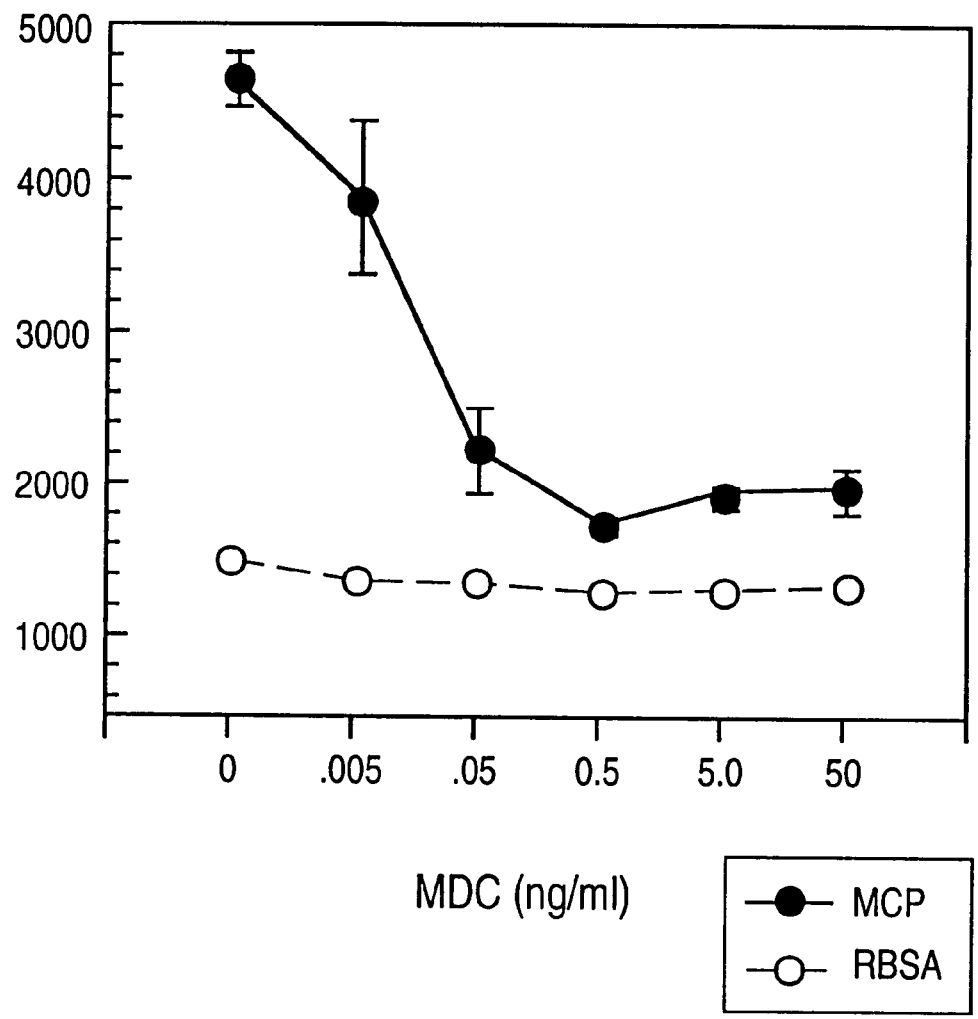
FIG. 6 is a graph depicting the chemotactic-inhibitory effect (measured in fluorescence units) of increasing concentrations of MDC on THP-1 monocyte migration induced by MCP-1. Closed circles depict the chemotactic-inhibitory effects of MDC where chemotaxis has been induced by MCP-1. Open circles depict the chemotactic-inhibitory effects of MDC in a control experiment wherein only the basal medium (RPMI with 0.2% BSA (RBSA), no MCP-1) was employed. The zero point on the x axis corresponds to the response of cells to MCP-1 and RBSA in the absence of any MDC.

The results of the chemotaxis assays with human mononuclear cells, presented in FIG. 2, suggested that MDC might inhibit cell migration. In the absence of MDC, monocytic THP-1 cells migrate to MCP-1, as shown in FIG. 6 (MDC of 0 ng/ml). However, when cells are exposed to MDC, the chemotactic response to MCP-1 (closed circles) is decreased. MDC, at concentrations of 0.005–0.5 ng/ml, inhibited monocyte chemotactic response to MCP-1. Although MDC inhibited the chemotactic response of monocytes to MCP-1, there was no significant effect of MDC on chemokinesis, or random migration, as reflected by the numbers of cells migrating to medium alone (open circles, RPMI with BSA), either in the presence of absence of MDC.

The inhibitory activity of MDC on monocyte chemotaxis indicates therapeutic utility for MDC in the treatment of several chronic inflammatory conditions (atherosclerosis, arthritis, pulmonary fibrosis) in which monocyte chemotaxis appears to play an important pathogenic role. Enhancing the activity of MDC in such diseases might result in the decreased migration of monocytes into tissues, thereby lessening the severity of disease symptoms.

EXAMPLE 14

MDC In Vivo Tumor Growth Inhibition Assay

Tumor growth-inhibition properties of MDC are assayed, e.g., by modifying the protocol described by Laning et al., *J. Immunol.*, 153: 4625–4635 (1994) for assaying the tumor growth-inhibitory properties of murine TCA3. An MDC-encoding cDNA is transfected by electroporation into the myeloma-derived cell line J558 (American Type Culture Collection, Rockville, Md.). Transfectants are screened for MDC production by standard techniques such as ELISA (enzyme-linked immunoadsorbant assay) using a monoclonal antibody generated against MDC as detailed in Example 18. A bolus of 10 million cells from an MDC-producing clone is injected subcutaneously into the lower right quadrant of BALB/c mice. For comparison, 10 million non-transfected cells are injected into control mice. The rate and frequency of tumor formation in the two groups is compared to determine efficacy of MDC in inhibiting tumor growth. The nature of the cellular infiltrate subsequently associated with the tumor cells is identified by histologic means. In addition, recombinant MDC (20 ng) is mixed with nontransfected J558 cells and injected (20 ng/day) into tumors derived from such cells, to assay the effect of MDC administered exogenously to tumor cells.

EXAMPLE 15

Intraperitoneal Injection Assay

The cells which respond to MDC in vivo are determined through injection of 1–1000 ng of purified MDC into the intraperitoneal cavity of mice or other mammals (e.g., rabbits or guinea pigs), as described by Luo et al., *J. Immunol.*, 153: 4616–4624 (1994). Following injection, leukocytes are isolated from peripheral blood and from the peritoneal cavity and identified by staining with the Diff Quick kit (Baxter, McGraw, Ill.). The profile of leukocytes is measured at various times to assess the kinetics of appearance of different cell types. In separate experiments, neutralizing antibodies directed against MDC (Example 18) are injected along with MDC to confirm that the infiltration of leukocytes is due to the activity of MDC.

EXAMPLE 16

In vivo Activity Assay - Subcutaneous Injection

The chemoattractant properties of MDC are assayed in vivo by adapting the protocol described by Meurer et al., *J. Exp. Med.*, 178: 1913–1921 (1993). Recombinant MDC (10–500 pmol/site) is injected intradermally into a suitable mammal, e.g., dogs or rabbits. At times of 4 to 24 hours, cell infiltration at the site of injection is assessed by histologic methods. The presence of MDC is confirmed by immunocytochemistry using antibodies directed against MDC. The nature of the cellular infiltrate is identified by staining with Baxter's Diff Quick kit.

EXAMPLE 17

Myelosuppression Activity Assays

The myelosuppressive activity of MDC is assayed by injection of MDC into mice or another mammal (e.g. rabbits, guinea pigs), e.g., as described by Maze et al., *J. Immunol.*, 149: 1004–1009 (1992) for the measurement of the myelosuppressive action of MIP-1α. A single dose of 0.2 to 10 µg of recombinant MDC is intravenously injected into C3H/HeJ mice (Jackson Laboratories, Bar Harbor Me.). The myelosuppressive effect of the chemokine is determined by measuring the cycling rates of myeloid progenitor cells in the femoral bone marrow and spleen. The suppression of growth and division of progenitor cells has clinical implications in the treatment of patients receiving chemotherapy or radiation therapy. The myeloprotective effect of such chemokine treatment has been demonstrated in pre-clinical models by Dunlop et al., *Blood*, 79: 2221 (1992).

An in vitro assay also is employed to measure the effect of MDC on myelosuppression, in the same manner as described previously for derivatives of the chemokines interleukin-8 (IL-8) and platelet factor 4 (PF-4). See Daly et al., *J. Biol. Chem.*, 270: 23282 (1995). Briefly, low density (less than 1.077 g/cm) normal human bone marrow cells are plated in 0.3% agar culture medium with 10% fetal bovine serum (HyClone, Logan, Utah) with 100 units/ml recombinant human GM-CSF (R&D Systems, Minneapolis, Minn.) plus 50 ng/ml recombinant human Steel factor (Immunex Corp., Seattle, Wash.) in the absence (control) and presence of MDC for assessment of granulocyte-macrophage precursors. For assessment of granulocyte erythroid myeloid megakaryocyte colony forming units (CFU-GEMM) and erythroid burst forming units (BFU-E), cells are grown in 0.9% methylcellulose culture medium in the presence of recombinant human erythropoietin (1–2 units/ml) in combination with 50 ng/ml Steel factor. Plates are scored for colonies after incubation at 37° C. in lowered (5%) $O_2$ for 14 days. The combination of GM-CSF and Steel factor or erythropoietin and Steel factor allow detection of large colonies (usually >1000 cells/colony) which come from early, more immature subsets of granulocyte myeloid colony forming units (CFU-GM), CFU-GEMM, and BFU-E.

EXAMPLE 18

Antibodies to Human MDC

A. Monoclonal antibodies

Recombinant MDC, produced by cleavage of a GST-MDC fusion protein as described in Example 6, was used to immunize a mouse for generation of monoclonal antibodies. In addition, a separate mouse was immunized with a chemically synthesized peptide corresponding to the N-termunus of the mature form of MDC (residues 1 to 12 of SEQ ID NO. 2). The peptide was synthesized on an Applied Biosystem Model 473A Peptide Synthesizer (Foster City, Calif.), and conjugated to Keyhole Lympet Hemocyanine (Pierce), according to the manufacturer's recommendations. For the initial injection, approximately 10 µg of MDC protein or conjugated peptide was emulsified with Freund's Complete Adjuvant and injected subcutaneously. At intervals of two to three weeks, additional aliquots of MDC protein were emulsified with Freund's Incomplete Adjuvant and injected subcutaneously. Prior to the final prefusion boost, a sample of serum was taken from the immunized mice. These sera were assayed by western blot to confirm their reactivity with MDC protein. For a prefusion boost, the mouse was injected with MDC in PBS, and four days later the mouse was sacrificed and its spleen removed. The spleen was placed in 10 ml serum-free RPMI 1640, and a single cell suspension was formed by grinding the spleen between the frosted ends of two glass microscope slides submerged in serum-free RPMI 1640, supplemented with 2 mM L-glutamine, 1 mM sodium pyruvate, 100 units/ml penicillin, and 100 μg/ml streptomycin (RPMI) (Gibco, Canada). The cell suspension was filtered through sterile 70-mesh Nitex cell strainer (Becton Dickinson, Parsippany, N.J.), and was washed twice by centrifuging at 200 g for 5 minutes and resuspending the pellet in 10 ml serum-free RPMI. Thymocytes taken from three naive Balb/c mice were prepared in a similar manner and used as a Feeder Layer. NS-1 myeloma cells, kept in log phase in RPMI with 10% fetal bovine serum (FBS) (Hyclone Laboratories, Inc., Logan, Utah) for three days prior to fusion, were centrifuged at 200 g for 5 minutes, and the pellet was washed twice as described in the foregoing paragraph.

Spleen cells ($2 \times 10^8$) were combined with $4 \times 10^7$ NS-1 cells and centrifuged, and the supernatant was aspirated. The cell pellet was dislodged by tapping the tube, and 2 ml of 37° C. PEG 1500 (50% in 75 mM Hepes, pH 8.0) (Boehringer Mannheim) was added with stirring over the course of 1 minute, followed by the addition of 14 ml of serum-free RPMI over 7 minutes. An additional 16 ml RPMI was added and the cells were centrifuged at 200 g for 10 minutes. After discarding the supernatant, the pellet was resuspended in 200 ml RPMI containing 15% FBS, 100 μM sodium hypoxanthine, 0.4 μM aminopterin, 16 μM thymidine (HAT) (Gibco), 25 units/ml IL-6 (Boehringer Mannheim) and 1.5× $10^6$ thymocytes/ml and plated into 10 Corning flat-bottom 96-well tissue culture plates (Corning, Corning N.Y.).

On days 2, 4, and 6, after the fusion, 100 μl of medium was removed from the wells of the fusion plates and replaced with fresh medium. On day 8, the fusion was screened by ELISA, testing for the presence of mouse IgG binding to MDC as follows, Immulon 4 plates (Dynatech, Cambridge, Mass.) were coated for 2 hours at 37° C. with 100 ng/well of MDC diluted in 25 mM Tris, pH 7.5.; The coating solution was aspirated and 200 μl/well of blocking solution [0.5% fish skin gelatin (Sigma) diluted in CMF-PBS] was added and incubated for 30 min. at 37° C. The blocking solution was aspirated and 50 μl culture supernatant was added. After incubation at 37° C. for 30 minutes, and washing three times with PBS containing 0.05% Tween 20 (PBST), 50 μl of horseradish peroxidase conjugated goat anti-mouse IgG(fc) (Jackson ImmunoResearch, West Grove, Pa.) diluted 1:7000 in PBST was added. Plates were incubated as above, washed four times with PBST, and 100 μL substrate, consisting of 1 mg/ml o-phenylene diamine (Sigma) and 0.1 μl/ml 30% $H_2O_2$ in 100 mM Citrate, pH 4.5, was added. The color reaction was stopped after 5 minutes with the addition of 50 μl of 15% $H_2SO_4$. $A_{490}$ was read on a plate reader (Dynatech).

Selected fusion wells were cloned twice by dilution into 96-well plates and visually scored for the number of colonies/well after 5 days. The monoclonal antibodies produced by hybridomas were isotyped using the Isostrip system (Boehringer Mannheim, Indianapolis, Ind.).

Anti-MDC antibodies were characterized further by western blotting against recombinant MDC produced as described above in *E. coli* or mammalian CHO cells. To prepare the blot, approximately 3 μl of sedimented cells (transformed *E. coli* producing MDC; transfected CHO cells producing MDC; untransformed *E. coli* (control); and untransfected CHO cells (control)) were dissolved in standard sample preparation buffer containing SDS (sodium dodecyl sulfate) and DTT (dithiolthreitol) (Sambrook et al.). After boiling, the lysates were fractionated via denaturing SDS-PAGE (18% acrylamide, Tris Glycine gel, NOVEX) and electroblotted to PVDF membranes (Millipore, Bedford, Mass.). MDC monoclonal antibodies were diluted to 0.7 μl/ml in PBS for use in the western blotting, following standard techniques (Sambrook et al.). As an additional control, the monoclonal antibodies were further tested for cross-reactivity on western blots of whole tissue lysates of human skin, tonsil, and thymus.

One anti-MDC monoclonal antibody, designated monoclonal antibody 191D, reacted strongly with recombinant MDC produced by both bacteria and mammalian cells. Further, this antibody displayed very little background reactivity against bacteria, the CHO mammalian cell line, or the whole human tissues tested. In addition, this antibody showed the ability to immunoprecipitate recombinant CHO-derived MDC, following standard immunoprecipitation protocols (Sambrook et al.).

The hybridoma cell line which produces monoclonal antibody 191D (designated hybridoma 191D) has been deposited with the American Type Culture Collection (ATCC), 12301 Parklawn Drive, Rockville Md. 20852 (USA) pursuant to the provisions of the Budapest Treaty (ATCC Deposit date: Jun. 4, 1996; ATCC Accession No. HB-12122). Availability of the deposited material is not to be construed as a license to practice the invention in contravention of the rights granted under the authority of any government in accordance with its patent laws.

B. Polyclonal antibodies.

Polyclonal antibodies against MDC were raised in rabbits following standard protocols (Sambrook et al.). Recombinant MDC produced as a GST fusion protein as described above was diluted in PBS, emulsified with Freund's Complete Adjuvant, and injected subcutaneously into rabbits. At intervals of three and six weeks, additional MDC diluted in PBS was emulsified with Freund's Incomplete Adjuvant and injected subcutaneously into the same rabbits. Ten days after the third immunization, serum was withdrawn from the rabbits and diluted ten-fold in Tris-buffered saline with 0.5% Tween 20 (TBS-T, Sambrook et al.) for characterization via western blotting against recombinant MDC as described above.

EXAMPLE 19

Calcium flux assay

Changes in intracellular calcium concentrations, indicative of cellular activation by chemokines, were monitored in several cell lines by an artrecognized calcium flux assay. Cells were incubated in 1 ml complete media containing 1 μM Fura-2/AM (Molecular Probes, Eugene, Oreg.) for 30 minutes at room temperature, washed once, and resuspended in D-PBS at ~$10^6$ cells/ml.

Two ml of suspended cells were placed in a continuously stirred cuvette at 37° C. in a fluorimeter (AMINCO-Bowman Series 2, Rochester, N.Y.). The concentration of intracellular calcium was indicated by fluorescence, which was monitored at 510 nm emission wavelength while switching between excitation wavelengths of 340 nm and 380 nm every 0.5 seconds. The ratio of the emissions from the 340 nm relative to the 380 mn excitation wavelengths corresponds to the level of intracellular calcium.

Cell lines measured by this assay included the following: the human embryonic kidney cell line HEK-293 stably transfected with the putative chemokine receptor gene V28 [Raport et al., *Gene,* 163: 295–299 (1995)]; HEK-293 cells stably transfected with the chemokine receptor gene CCR5 [Samson et al., *Biochemistry,* 35: 3362–3367 (1996); see also co-owned, co-pending U.S. patent application Ser. No. 08/575,967, filed Dec. 20, 1995, incorporated herein by reference, disclosing chemokine receptor materials and methods, including CCR5 (identified therein as "88C")], the human monocytic cell line THP-1, the human lung epithelial cell line A-549; and the human fibroblast cell line IMR-90. None of these cell lines fluxed calcium in response to the recombinant MDC protein. As positive controls, the HEK-293 transfectants responded strongly to thrombin, indicating that the assay was valid. In addition, the THP-1 cells responded strongly to the commercially available chemokines MCP-1 and MCP-3 (Peprotech, Rocky Hill, N.J.) at a final concentration of 25 ng/ml. No additional stimuli were tested on the A-549 or IMR-90 cell lines.

EXAMPLE 20

Inhibition of HIV proliferation

Several CC chemokines have been implicated in suppressing the proliferation of Human Immunodeficiency Virus (HIV), the causative agent of human Acquired Immune Deficiency Syndrome (AIDS). See Cocchi et al., *Science,* 270: 1811 (1995). The HIV antiproliferative activity of MDC is measured by means such as those described by Cocchi et al., in which a $CD4^+$ T cell line is acutely infected with an HIV strain and cultured in the presence of various concentrations of MDC. After three days, a fresh dilution of MDC in the culture medium is added to the cells. At 5 to 7 days following infection, the level of HIV is measured by testing the culture supernatants for the presence of HIV p24 antigen by a commercial ELISA test (Coulter, Miami, Fla.).

Antibodies against MDC are tested for their ability to neutralize the suppressive activity produced by human lymphocytes (Cocchi, supra). In addition, the efficacy of chemically synthesized MDC analogs (Ex. 11) or analogs produced by recombinant methods is also tested in assays of HIV inhibition.

EXAMPLE 21

Effects of MDC on Fibroblast Proliferation

In addition to their ability to attract and activate leukocytes, some chemokines, such as IL-8, have been shown to be capable of affecting the proliferation of non-leukocytic cells [see Tuschil, *J. Invest. Dermatol.,* 99: 294–298 (1992)]. Fibroblasts throughout the body are important to the structural integrity of most tissues. The proliferation of fibroblasts is essential to wound healing and response to injury but can be deleterious as well, as in the case of chronic inflammatory diseases, such as pulmonary fibrosis [Phan, in: *Immunology of Inflammation,* Elsevier (1983), pp. 121–162].

In vitro cell proliferation assays were utilized to assess the effects of MDC on the proliferation of fibroblasts. Human fibroblasts (CRL-1635) were obtained from ATCC and maintained in culture in DMEM with 10% FBS and 1% antibiotics. Proliferation assays were performed and quantitated as previously described in the art by Denholm and Phan, *Amer. J. Pathol.,* 134: 355–363 (1989). Briefly, on day 1, $2.5 \times 10^3$ cells/well were plated into 96 well plates in DMEM with 10% FBS. Day 2: twenty-four hours after plating, medium on cells was changed to serum-free DMEM. Day 3: medium was removed from cells and replaced with MDC diluted in DMEM containing 0.4% FBS. Day 5: one microCurie of $^3$H-thymidine was added per well and incubation continued for an additional 5 hours. Cells were harvested onto glass fiber filters. Cell proliferation was expressed as cpm of $^3$H-thymidine incorporated into fibroblasts. Controls for this assay included the basal medium for this assay, DMEM with 0.4% FBS as the negative control, and DMEM with 10% FBS as the positive control.

Figure 7:
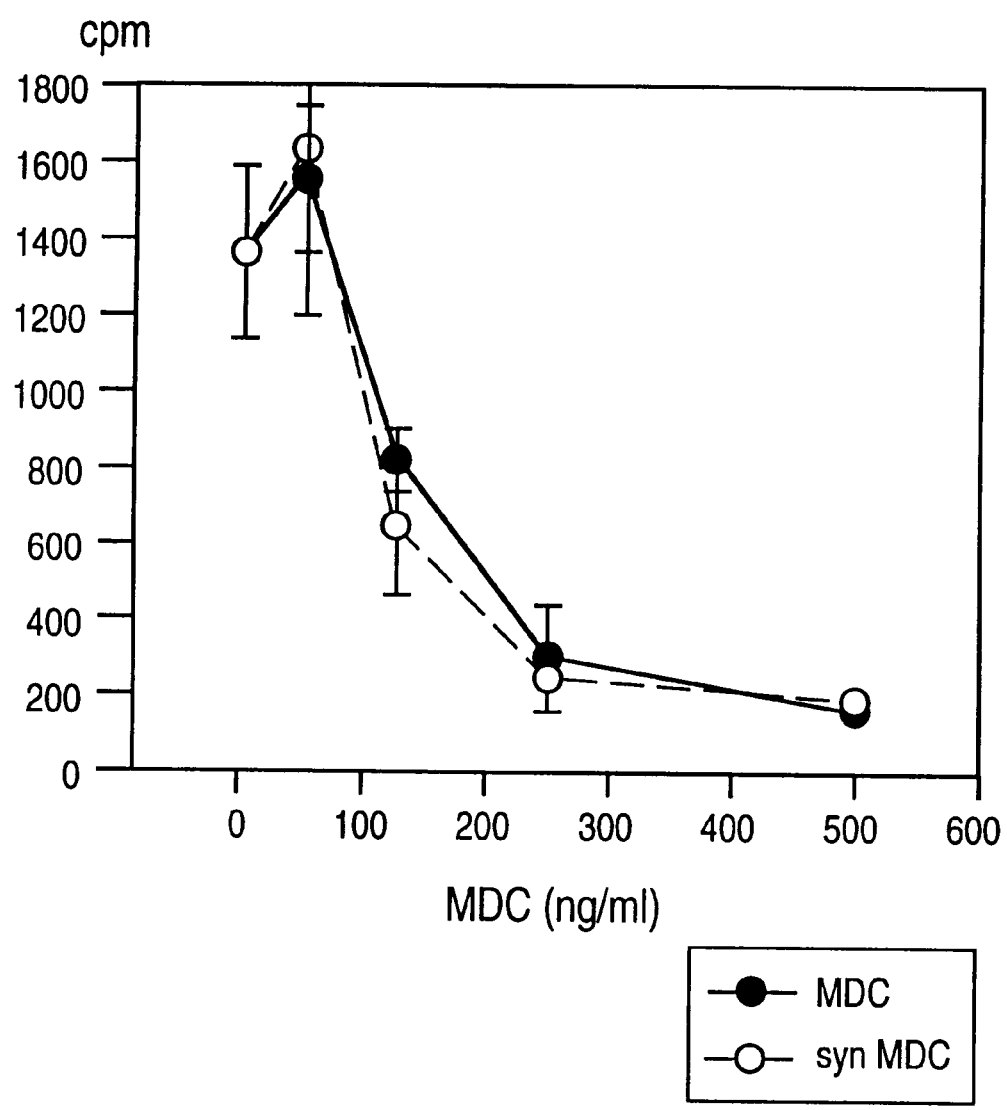
FIG. 7 is a graph depicting the effect (measured in counts per minute (cpm)) of increasing concentrations of MDC on fibroblast proliferation. Closed circles depict the proliferative response with purified MDC that was recombinantly produced in CHO cells (Example 10F). Open circles depict the response with chemically synthesized MDC (Example 11).

As shown in FIG. 7, MDC treatment decreased the proliferation of fibroblasts in a dose dependent manner. Similar inhibition of fibroblast proliferation was observed with both MDC purified from CHO cells (closed circles) and chemically synthesized MDC (open circles). The fibroblast-antiproliferative effect of MDC indicates a therapeutic utility for MDC in the treatment of diseases such as pulmonary fibrosis and tumors, in which enhanced or uncontrolled cell proliferation is a major feature.

EXAMPLE 22

Cell Proliferation Assays

The effects of MDC upon the proliferation of epithelial cells, T cells, fibroblasts, endothelial cells, macrophages, and tumor cells are assayed by methods known in the art, such as those described in Denholm et al., *Amer. J. Pathol.,* 134: 355–363 (1989), and "In Vitro Assays of Lymphocyte Functions," in: *Current Protocols Immunology,* Sections 3–4, Wiley and Sons (1992), for the assay of growth factor activities. In these methods, enhancement or inhibition of cell growth and the release of growth factors are measured.

MDC effects on the proliferation of epithelial cells and endothelial cells are assayed using the same procedures as those described above for fibroblasts (Example 21).

The effects on the proliferation of T cells are determined using peripheral blood lymphocytes. Mononuclear cells are isolated from peripheral blood as described in Denholm et al., *Amer. J. Pathol.,* 135: 571–580 (1989); cells are resuspended in RPMI with 10% FBS and incubated overnight in plastic tissue culture flasks. Lymphocytes remain in suspension in these cultures and are obtained by centrifugation of culture medium. One hundred thousand lymphocytes are plated into each well of a 96 well plate and incubated for three days in medium (RPMI plus 10% FBS) containing 1 µg/ml PHA with or without 50, 125, 250 or 500 ng/ml of MDC. One microCurie of $^3$H-thymidine is added during the last 18 hours of incubation. Cells are harvested and proliferations expressed as described for fibroblasts in Example 21.

The effects of MDC on macrophage proliferation are determined using elicited guinea pig peritoneal macrophages, obtained as described above in Example 13. Macrophages are plated into 96 well plates at a density of one hundred thousand cells per well in RPMI with 10% FBS, and incubated 2 hours to allow cells to adhere. Medium is then removed and replaced with fresh medium with or without 50, 125, 250 or 500 ng/ml of MDC. Cells with MDC are incubated three days, and proliferation is determined as described above for lymphocytes.

Chemokine-mediated control of the proliferation of these cell types has therapeutic implications in enhancing tissue repair following injury, and in limiting the proliferation of these cells in chronic inflammatory reactions such as psoriasis, fibrosis, and atherosclerosis, and in neoplastic conditions.

EXAMPLE 23

In Vivo Fibroblast Proliferation Assay

The anti-proliferative effects of MDC upon fibroblasts are determined in vivo by the methods known in the art, such as those reported by Phan and Fantone, Amer. J. Pathol., 50: 587–591 (1984), which utilize a rat model of pulmonary fibrosis in which the disease is induced by bleomycin. This model is well-characterized and allows for the assessment of fibroblast proliferation and collagen synthesis during all stages of this disease.

Briefly, rats are divided into four treatment groups: 1) controls, given intratracheal injections of normal saline; 2) saline-injected rats which also receive a daily intraperitoneal injection of 500 ng of MDC in saline; 3) bleomycin-treated, given an intratracheal injection of 1.5 mg/kg bleomycin (Calbiochem, Palo Alto, Calif.); and 4) bleomycin-treated rats which also are given a daily intraperitoneal injection of 500 ng of MDC.

Three rats per group are sacrificed at 4, 7, 14, 21, and 28 days after the initial intratracheal injections. Lungs are removed and samples of each lobe taken for histological examination and assays of collagen content.

EXAMPLE 24

MDC Modulator Assays

Modulators of MDC activity may be useful for the treatment of diseases or symptoms of diseases wherein MDC plays a role. Such modulators may be either agonists or antagonists of MDC binding. The following receptor binding assays provide procedures for identifying such MDC modulators.

MDC is labeled with a detectable label such as $^{125}I$, $^{3}H$, $^{14}C$, biotin, or Europium. A preparation of cell membranes containing MDC receptors is prepared from natural cells that respond to MDC, such as human macrophages, phorbol ester-stimulated THP-1 cells, human fibroblasts, human fibroblast cell lines, or guinea pig macrophages. (Alternatively, a recombinant receptor preparation is made from cells transfected with an MDC receptor cDNA, when such an MDC receptor cDNA is identified and cloned.) The membrane preparation is exposed to $^{125}I$-labeled MDC, for example, and incubated under suitable conditions (e.g., ten minutes at 37° C.). The membranes, with any bound $^{125}I$-MDC, are then collected on a filter by vacuum filtration and washed to remove unbound $^{125}I$-MDC. The radioactivity associated with the bound MDC is then quantitated by subjecting the filters to liquid scintillation spectrophotometry.

The specificity of MDC binding may be confirmed by repeating the foregoing assay in the presence of increasing quantities of unlabelled MDC, and measuring the level of competition for binding to the receptor. These binding assays also can be employed to identify modulators of MDC receptor binding.

The foregoing receptor binding assay also may be performed with the following modification: in addition to labeled MDC, a potential MDC modulator is exposed to the membrane preparation. In this assay variation, an increased level (quantity) of membrane-amodulator is an activator of MDC bntial modulator is an activator of MDC binding; a decreased level (quantity) of membrane-associated label indicates the potential modulator is an inhibitor of MDC receptor binding. This assay can be utilized to identify specific activators and inhibitors of MDC binding from large libraries of chemical compounds or natural products. Rapid screening of multiple modulator candidate compounds simultaneously is specifically contemplated.

The biological functions of MDC, elucidated as described above, suggest several clinical applications.

Chemokines in general attract and activate monocytes and macrophages (Baggiolini et al., supra), and MDC in particular attracts macrophages and inhibits monocyte chemotaxis. Thus, MDC expression in a pathogenic inflammatory setting may exacerbate disease states by recruiting additional macrophages or other leukocytes to the disease site, by activating the leukocytes that are already there, or by inducing leukocytes to remain at the site. Thus, inhibiting the chemoattractant activity of MDC may be expected to alleviate deleterious inflammatory processes. Significantly, the potential benefits of such an approach have been directly demonstrated in experiments involving IL-8, a C-X-C chemokine that attracts and activates neutrophils. Antibodies directed against IL-8 have a profound ability to inhibit inflammatory disease mediated by neutrophils [Harada et al., J. Leukoc. Biol., 56: 559 (1994)]. Inhibition of MDC is expected to have a similar effect in diseases in which macrophages are presumed to play a role, e.g., Crohn's disease, rheumatoid arthritis, or atherosclerosis.

Alternatively, augmenting the effect of MDC may have a beneficial role in such diseases, as chemokines have also been shown to have a positive effect in wound healing and angiogenesis. Thus, exogenous MDC or MDC agonists may be beneficial in promoting recovery from such diseases.

In addition, the myelosuppressive effect demonstrated for the C—C chemokine MIP-1α (Maze et al., supra) suggests that MDC may have a similar activity. Such activity, provided by MDC or MDC agonists, may yield substantial benefits for patients receiving chemotherapy or radiation therapy, reducing the deleterious effects of the therapy on the patient's myeloid progenitor cells.

MDC or MDC agonists may also prove to be clinically important in the treatment of tumors, as suggested by the ability of the C—C chemokine TCA3 to inhibit tumor formation in mice (see Laning et al., supra). MDC may act directly or indirectly to inhibit tumor formation, e.g., by attracting and activating various non-specific effector cells to the tumor site or by stimulating a specific anti-tumor immunity. The fibroblast-antiproliferative effect of MDC indicates a therapeutic utility for MDC in the treatment of diseases such as pulmonary fibrosis and tumors, in which enhanced or uncontrolled cell proliferation is a major feature.

While the present invention has been described in terms of specific embodiments, it is understood that variations and modifications will occur to those skilled in the art. Accordingly, only such limitations as appear in the appended claims should be placed on the invention.

What is claimed is:

1. A polypeptide that is capable of inhibiting MDC-induced chemotaxis comprising amino acids 1 to 70 of SEQ ID NO: 30.

2. A purified polypeptide having an amino acid sequence that comprises amino acids 1–69 of SEQ ID NO: 2, and that further comprises at least one additional amino terminal amino acid, wherein the amino acid sequence of said polypeptide is not identical to amino acids −24 to 69 of SEQ ID NO: 2 and wherein said polypeptide is capable of inhibiting MDC-induced chemotaxis.

3. A polypeptide according to claim 2 comprising amino acids 1 to 70 of SEQ ID NO: 30.

4. A polypeptide according to claim 2 having an amino acid sequence consisting of positions 1 to 70 of SEQ ID NO: 30.

5. A pharmaceutical composition comprising a polypeptide according to any one of claims 1, 2, 3 and 4, in a pharmaceutically acceptable carrier.

* * * * *

UNITED STATES PATENT AND TRADEMARK OFFICE
CERTIFICATE OF CORRECTION

PATENT NO.    : 5,932,703
DATED         : August 3, 1999
INVENTOR(S)   : Godiska et al.

It is certified that error appears in the above-identified patent and that said Letters Patent is hereby corrected as shown below:

Title page,
Item [56], References Cited, OTHER PUBLICATIONS, "Becker et al.," reference, delete "bronchaolveolar" and insert -- bronchoalveolar --.
"Brown et al.," reference, "Process" and insert -- Processes --.
"Cocchi et al., reference, delete "Rantes" and insert -- RANTES --.
"Danoff et al.," reference, delete "Rantes" and insert -- RANTES --.
"Frömmel et al.," reference, delete "of the Rate of" and insert -- on the Rate of --.
"Howard et al.," reference, delete "therapuetic" and insert -- therapeutic --.
"Kuna et al.," reference, delete "Rantes" and insert -- RANTES -- and
 delete "(Jul. 15, 1993)."
"Kurjan et al.," reference, delete "Peromone" and insert -- Pheromone --
and delete "Precurson" and insert -- Precursor --
"Major and Hamilton," reference, delete "Devense" and insert -- Defense --.
"Meurer et al.," reference, delete "Rantes" and insert -- RANTES --.
"Peri et al.," reference, delete "Elisa" and insert -- ELISA --.
"Stafforni et al.," reference, delete "Stafforni" and insert -- Stafforini --.

Column 2,
Line 63, delete "MIP-*" and insert -- MIP-1* --.

Column 10,
Line 53, delete "CDNA" and insert -- cDNA --.

Column 12,
Lines 1-2, delete "CACCGGATCCTCATTGGCTCAGCTATTGAGAA" and insert
 -- CACCGGATCCTCATTGGCTCAGCTTATTGAGAA --.
Line 43, delete "preciptated" and insert -- precipitated --.

UNITED STATES PATENT AND TRADEMARK OFFICE
CERTIFICATE OF CORRECTION

PATENT NO.    : 5,932,703
DATED         : August 3, 1999
INVENTOR(S)   : Godiska et al.

It is certified that error appears in the above-identified patent and that said Letters Patent is hereby corrected as shown below:

Column 20,
Line 17, delete "Kujan" and insert -- Kurjan --.

Column 21,
Line 13, delete "(In Vitrogen," and insert -- (Invitrogen, --.

Column 22,
Line 36, delete "Hindil" and insert -- Hind III --.

Column 23,
Line 23, delete "form" and insert -- from --.

Column 24,
Line 7, delete "L-Phenylainine" and insert -- L-Phenylalanine --.

Column 25,
Line 9, delete "-Sepaharose" and insert -- Sepharose --.

Column 26,
Line 52, delete "iysine" and insert -- lysine --.

Column 29,
Line 42, delete "Ctometry" and insert -- Cytometry --.

Column 31,
Line 8, delete "presence of absence of" and insert -- presence or absence of --.

Column 35,
Line 4, delete "380 mn" and insert -- 380 nm --.

UNITED STATES PATENT AND TRADEMARK OFFICE
CERTIFICATE OF CORRECTION

PATENT NO. : 5,932,703
DATED : August 3, 1999
INVENTOR(S) : Godiska et al.

It is certified that error appears in the above-identified patent and that said Letters Patent is hereby corrected as shown below:

Column 38,
Lines 3-4, delete "membrane-amodulator is an activator of MDC bntial modulator is an activator of MDC binding;" and insert -- membrane associated label indicates the potential modulator is an activator of MDC binding; --.

Column 53,
Lines 5 and 25, delete "MIP-1" and insert -- MIP-1* --.

Signed and Sealed this

Third Day of August, 2004

JON W. DUDAS
*Acting Director of the United States Patent and Trademark Office*

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
        (A) LENGTH: 2923 base pairs
        (B) TYPE: nucleic acid
        (C) STRANDEDNESS: single
        (D) TOPOLOGY: linear (ii) MOLECULE TYPE: protein (ix) FEATURE:
        (A) NAME/KEY: CDS
        (B) LOCATION: 20..298

(ix) FEATURE:
        (A) NAME/KEY: mat_peptide
        (B) LOCATION: 92..298

(xi) SEQUENCE DESCRIPTION: SEQ ID NO:1:

```
GAGACATACA GGACAGAGC ATG GCT CGC CTA CAG ACT GCA CTC CTG GTT GTC        52
                    Met Ala Arg Leu Gln Thr Ala Leu Leu Val Val
                    -24              -20                 -15

CTC GTC CTC CTT GCT GTG GCG CTT CAA GCA ACT GAG GCA GGC CCC TAC        100
Leu Val Leu Leu Ala Val Ala Leu Gln Ala Thr Glu Ala Gly Pro Tyr
            -10                  -5                  1

GGC GCC AAC ATG GAA GAC AGC GTC TGC TGC CGT GAT TAC GTC CGT TAC        148
Gly Ala Asn Met Glu Asp Ser Val Cys Cys Arg Asp Tyr Val Arg Tyr
        5                   10                  15

CGT CTG CCC CTG CGC GTG GTG AAA CAC TTC TAC TGG ACC TCA GAC TCC        196
Arg Leu Pro Leu Arg Val Val Lys His Phe Tyr Trp Thr Ser Asp Ser
20                  25                  30                  35

TGC CCG AGG CCT GGC GTG GTG TTG CTA ACC TTC AGG GAT AAG GAG ATC        244
Cys Pro Arg Pro Gly Val Val Leu Leu Thr Phe Arg Asp Lys Glu Ile
                40                  45                  50

TGT GCC GAT CCC AGA GTG CCC TGG GTG AAG ATG ATT CTC AAT AAG CTG        292
Cys Ala Asp Pro Arg Val Pro Trp Val Lys Met Ile Leu Asn Lys Leu
            55                  60                  65

AGC CAA TGAAGAGCCT ACTCTGATGA CCGTGGCCTT GGCTCCTCCA GGAAGGCTCA         348
Ser Gln

GGAGCCCTAC CTCCCTGCCA TTATAGCTGC TCCCCGCCAG AAGCCTGTGC CAACTCTCTG       408

CATTCCCTGA TCTCCATCCC TGTGGCTGTC ACCCTTGGTC ACCTCCGTGC TGTCACTGCC       468

ATCTCCCCCC TGACCCCTCT AACCCATCCT CTGCCTCCCT CCCTGCAGTC AGAGGGTCCT       528

GTTCCCATCA GCGATTCCCC TGCTTAAACC CTTCCATGAC TCCCCACTGC CCTAAGCTGA       588

GGTCAGTCTC CCAAGCCTGG CATGTGGCCC TCTGGATCTG GGTTCCATCT CTGTCTCCAG       648

CCTGCCCACT TCCCTTCATG AATGTTGGGT TCTAGCTCCC TGTTCTCCAA ACCCATACTA       708

CACATCCCAC TTCTGGGTCT TTGCCTGGGA TGTTGCTGAC ACTCAGAAAG TCCCACCACC       768

TGCACATGTG TAGCCCCACC AGCCCTCCAA GGCATTGCTC GCCCAAGCAG CTGGTAATTC       828

CATTTCATGT ATTAGATGTC CCCTGGCCCT CTGTCCCCTC TTAATAACCC TAGTCACAGT       888

CTCCGCAGAT TCTTGGGATT TGGGGGTTTT CTCCCCCACC TCTCCACTAG TTGGACCAAG       948

GTTTCTAGCT AAGTTACTCT AGTCTCCAAG CCTCTAGCAT AGAGCACTGC AGACAGGCCC      1008

TGGCTCAGAA TCAGAGCCCA GAAAGTGGCT GCAGACAAAA TCAATAAAAC TAATGTCCCT      1068

CCCCTCTCCC TGCCAAAAGG CAGTTACATA TCAATACAGA GACTCAAGGT CACTAGAAAT      1128
```

```
GGGCCAGCTG GGTCAATGTG AAGCCCCAAA TTTGCCCAGA TTCACCTTTC TTCCCCCACT    1188

CCCTTTTTTT TTTTTTTTTT TTTGAGATGG AGTTTCGCTC TTGTCACCCA CGCTGGAGTG    1248

CAATGGTGTG GTCTTGGCTT ATTGAAGCCT CTGCCTCCTG GGTTCAAGTG ATTCTCTTGC    1308

CTCAGCCTCC TGAGTAGCTG GGATTACAGG TTCCTGCTAC CACGCCCAGC TAATTTTTGT    1368

ATTTTTAGTA GAGACGAGGC TTCACCATGT TGGCCAGGCT GGTCTCGAAC TCCTGTCCTC    1428

AGGTAATCCG CCCACCTCAG CCTCCCAAAG TGCTGGGATT ACAGGCGTGA GCCACAGTGC    1488

CTGGCCTCTT CCCTCTCCCC ACTGCCCCCC CCAACTTTTT TTTTTTTTTT ATGGCAGGGT    1548

CTCACTCTGT CGCCCAGGCT GGAGTGCAGT GGCGTGATCT CGGCTCACTA CAACCTCGAC    1608

CTCCTGGGTT CAAGTGATTC TCCCACCCCA GCCTCCCAAG TAGCTGGGAT TACAGGTGTG    1668

TGCCACTACG GCTGGCTAAT TTTTGTATTT TTAGTAGAGA CAGGTTTCAC CATATTGGCC    1728

AGGCTGGTCT TGAACTCCTG ACCTCAAGTG ATCCACCTTC CTTGTGCTCC CAAAGTGCTG    1788

AGATTACAGG CGTGAGCTAT CACACCCAGC CTCCCCCTTT TTTTCCTAAT AGGAGACTCC    1848

TGTACCTTTC TTCGTTTTAC CTATGTGTCG TGTCTGCTTA CATTTCCTTC TCCCCTCAGG    1908

CTTTTTTTGG GTGGTCCTCC AACCTCCAAT ACCCAGGCCT GGCCTCTTCA GAGTACCCCC    1968

CATTCCACTT TCCCTGCCTC CTTCCTTAAA TAGCTGACAA TCAAATTCAT GCTATGGTGT    2028

GAAAGACTAC CTTTGACTTG GTATTATAAG CTGGAGTTAT ATATGTATTT GAAAACAGAG    2088

TAAATACTTA AGAGGCCAAA TAGATGAATG AAGAATTTT AGGAACTGTG AGAGGGGAC     2148

AAGGTGAAGC TTTCCTGGCC CTGGGAGGAA GCTGGCTGTG GTAGCGTAGC GCTCTCTCTC    2208

TCTGTCTGTG GCAGGAGCCA AGAGTAGGG TGTAATTGAG TGAAGGAATC CTGGGTAGAG     2268

ACCATTCTCA GGTGGTTGGG CCAGGCTAAA GACTGGGAGT TGGGTCTATC TATGCCTTTC    2328

TGGCTGATTT TTGTAGAGAC GGGGTTTTGC CATGTTACCC AGGCTGGTCT CAAACTCCTG    2388

GGCTCAAGCG ATCCTCCTGG CTCAGCCTCC CAAAGTGCTG GGATTACAGG CGTGAATCAC    2448

TGCGCCTGGC TTCCTCTTCC TCTTGAGAAA TATTCTTTTC ATACAGCAAG TATGGGACAG    2508

CAGTGTCCCA GGTAAAGGAC ATAAATGTTA CAAGTGTCTG GTCCTTTCTG AGGGAGGCTG    2568

GTGCCGCTCT GCAGGGTATT TGAACCTGTG GAATTGGAGG AGGCCATTTC ACTCCCTGAA    2628

CCCAGCCTGA CAAATCACAG TGAGAATGTT CACCTTATAG GCTTGCTGTG GGCTCAGGT     2688

TGAAAGTGTG GGGAGTGACA CTGCCTAGGC ATCCAGCTCA GTGTCATCCA GGGCCTGTGT    2748

CCCTCCCGAA CCCAGGGTCA ACCTGCCTGC ACAGGCACT AGAAGGACGA ATCTGCCTAC     2808

TGCCCATGAA CGGGGCCCTC AAGCGTCCTG GGATCTCCTT CTCCCTCCTG TCCTGTCCTT    2868

GCCCCTCAGG ACTGCTGGAA AATAAATCCT TTAAAATAGT AAAAAAAAAA AAAAA         2923
```

(2) INFORMATION FOR SEQ ID NO:2:

(i) SEQUENCE CHARACTERISTICS:
        (A) LENGTH: 93 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Arg Leu Gln Thr Ala Leu Leu Val Leu Val Leu Leu Ala
-24             -20                 -15                 -10

Val Ala Leu Gln Ala Thr Glu Ala Gly Pro Tyr Gly Ala Asn Met Glu
            -5                  1               5

Asp Ser Val Cys Cys Arg Asp Tyr Val Arg Tyr Arg Leu Pro Leu Arg
```

```
            10                  15                  20
Val Val Lys His Phe Tyr Trp Thr Ser Asp Ser Cys Pro Arg Pro Gly
 25                  30                  35                  40

Val Val Leu Leu Thr Phe Arg Asp Lys Glu Ile Cys Ala Asp Pro Arg
             45                  50                  55

Val Pro Trp Val Lys Met Ile Leu Asn Lys Leu Ser Gln
                 60                  65
```

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

GACACTATAG AATAGGGC                                               18

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

GTAAAACGAC GGCCAGT                                                17

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

AATTAACCCT CACTAAAGGG                                        20

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GTAATACGAC TCACTATAGG GC                                  22

(2) INFORMATION FOR SEQ ID NO:7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TCTATCTAGA GGCCCCTACG GCGCCAACAT GGAAG                                    35

(2) INFORMATION FOR SEQ ID NO:8:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:8:

CACCGGATCC TCATTGGCTC AGCTTATTGA GAA                                      33

(2) INFORMATION FOR SEQ ID NO:9:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:9:

AATGGATCCA CAGCACGGAG GTGACCAAG                                           29

(2) INFORMATION FOR SEQ ID NO:10:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:10:

AGTCAAGCTT AGGGCACTCT GGGATCGGCA C                                        31

(2) INFORMATION FOR SEQ ID NO:11:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:11:

TATCGGATCC TGGTTCCGCG TGGCCCCTAC GGCGCCAACA TGGAA                         45

(2) INFORMATION FOR SEQ ID NO:12:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:12:

GAAATCCAGC AAGTATATAG CA                                                  22

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

```
ATTGCCATGG CCGGCCCCTA CGGCGCCAAC ATGGAA                               36
```

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

```
GACCAAGCTT GAGACATACA GGACAGAGCA                                     30
```

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

```
TGGATCTAGA AGTTGGCACA GGCTTCTGG                                      29
```

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

```
CGAAATTAAT ACGACTCACT                                                20
```

(2) INFORMATION FOR SEQ ID NO:17:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

```
TGGATCTAGA TCAATTCAAG TCCTCCTCGC TGATCAGCTT CTGCTCTTGG CTCAGCTTAT     60

TGAGAAT                                                              67
```

(2) INFORMATION FOR SEQ ID NO:18:

(i) SEQUENCE CHARACTERISTICS:
    (A) LENGTH: 99 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: misc_feature
    (D) OTHER INFORMATION: "Hu MCP-3"

(ix) FEATURE:
    (A) NAME/KEY: Protein
    (B) LOCATION: 1..76

(xi) SEQUENCE DESCRIPTION: SEQ ID NO:18:

Met Lys Ala Ser Ala Ala Leu Leu Cys Leu Leu Leu Thr Ala Ala Ala
            -20                 -15                 -10

Phe Ser Pro Gln Gly Leu Ala Gln Pro Val Gly Ile Asn Thr Ser Thr
         -5                  1                   5

Thr Cys Cys Tyr Arg Phe Ile Asn Lys Lys Ile Pro Lys Gln Arg Leu
 10              15                  20                  25

Glu Ser Tyr Arg Arg Thr Thr Ser Ser His Cys Pro Arg Glu Ala Val
                 30                  35                  40

Ile Phe Lys Thr Lys Leu Asp Lys Glu Ile Cys Ala Asp Pro Thr Gln
             45                  50                  55

Lys Trp Val Gln Asp Phe Met Lys His Leu Asp Lys Lys Thr Gln Thr
             60                  65                  70

Pro Lys Leu
     75

(2) INFORMATION FOR SEQ ID NO:19:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc_feature
        (D) OTHER INFORMATION: "Hu MCP-1"

(ix) FEATURE:
        (A) NAME/KEY: Protein
        (B) LOCATION: 1..76

(xi) SEQUENCE DESCRIPTION: SEQ ID NO:19:

Met Lys Val Ser Ala Ala Leu Leu Cys Leu Leu Leu Ile Ala Ala Thr
            -20                 -15                 -10

Phe Ile Pro Gln Gly Leu Ala Gln Pro Asp Ala Ile Asn Ala Pro Val
         -5                  1                   5

Thr Cys Cys Tyr Asn Phe Thr Asn Arg Lys Ile Ser Val Gln Arg Leu
 10              15                  20                  25

Ala Ser Tyr Arg Arg Ile Thr Ser Ser Lys Cys Pro Lys Glu Ala Val
                 30                  35                  40

Ile Phe Lys Thr Ile Val Ala Lys Glu Ile Cys Ala Asp Pro Lys Gln
             45                  50                  55

Lys Trp Val Gln Asp Ser Met Asp His Leu Asp Lys Gln Thr Gln Thr
             60                  65                  70

Pro Lys Thr

75

(2) INFORMATION FOR SEQ ID NO:20:

(i) SEQUENCE CHARACTERISTICS:
        (A) LENGTH: 76 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc_feature
        (D) OTHER INFORMATION: "Hu MCP-2"

(xi) SEQUENCE DESCRIPTION: SEQ ID NO:20:

```
Gln Pro Asp Ser Val Ser Ile Pro Ile Thr Cys Cys Phe Asn Val Ile
  1               5                  10                  15
Asn Arg Lys Ile Pro Ile Gln Arg Leu Glu Ser Tyr Thr Arg Ile Thr
             20                  25                  30
Asn Ile Gln Cys Pro Lys Glu Ala Val Ile Phe Lys Thr Lys Arg Gly
         35                  40                  45
Lys Glu Val Cys Ala Asp Pro Lys Glu Arg Trp Val Arg Asp Ser Met
 50                  55                  60
Lys His Leu Asp Gln Ile Phe Gln Asn Leu Lys Pro
 65                  70                  75
```

(2) INFORMATION FOR SEQ ID NO:21:

(i) SEQUENCE CHARACTERISTICS:
        (A) LENGTH: 91 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc_feature
        (D) OTHER INFORMATION: "RANTES"

(ix) FEATURE:
        (A) NAME/KEY: Protein
        (B) LOCATION: 1..68

(xi) SEQUENCE DESCRIPTION: SEQ ID NO:21:

```
Met Lys Val Ser Ala Ala Ala Leu Ala Val Ile Leu Ile Ala Thr Ala
            -20                 -15                 -10
Leu Cys Ala Pro Ala Ser Ala Ser Pro Tyr Ser Ser Asp Thr Thr Pro
         -5                   1                   5
Cys Cys Phe Ala Tyr Ile Ala Arg Pro Leu Pro Arg Ala His Ile Lys
 10                  15                  20                  25
Glu Tyr Phe Tyr Thr Ser Gly Lys Cys Ser Asn Pro Ala Val Val Phe
                 30                  35                  40
Val Thr Arg Lys Asn Arg Gln Val Cys Ala Asn Pro Glu Lys Lys Trp
             45                  50                  55
Val Arg Glu Tyr Ile Asn Ser Leu Glu Met Ser
             60                  65
```

(2) INFORMATION FOR SEQ ID NO:22:

(i) SEQUENCE CHARACTERISTICS:
        (A) LENGTH: 91 amino acids
        (B) TYPE: amino acid
        (C) STRANDEDNESS: single (D) TOPOLOGY: linear (ii) MOLECULE TYPE: peptide (ix) FEATURE:
        (A) NAME/KEY: misc_feature
        (D) OTHER INFORMATION: "MIP-1 "

(ix) FEATURE:
        (A) NAME/KEY: Protein
        (B) LOCATION: 1..68

(xi) SEQUENCE DESCRIPTION: SEQ ID NO:22:

Met Lys Leu Cys Val Thr Val Leu Ser Leu Leu Met Leu Val Ala Ala
        -20                 -15                 -10

Phe Cys Ser Pro Ala Leu Ser Ala Pro Met Gly Ser Asp Pro Pro Thr
        -5                  1                   5

Ala Cys Cys Phe Ser Tyr Thr Arg Glu Ala Ser Ser Asn Phe Val Val
 10              15                  20                  25

Asp Tyr Tyr Glu Thr Ser Ser Leu Cys Ser Gln Pro Ala Val Val Phe
                30                  35                  40

Gln Thr Lys Arg Ser Lys Gln Val Cys Ala Asp Pro Ser Glu Ser Trp
                45                  50                  55

Val Gln Glu Tyr Val Tyr Asp Leu Glu Leu Asn
        60                  65

(2) INFORMATION FOR SEQ ID NO:23:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: misc_feature
        (D) OTHER INFORMATION: "MIP-1'"

(ix) FEATURE:
        (A) NAME/KEY: Protein
        (B) LOCATION: 1..70

(xi) SEQUENCE DESCRIPTION: SEQ ID NO:23:

Met Gln Val Ser Thr Ala Ala Leu Ala Val Leu Leu Cys Thr Met Ala
        -20                 -15                 -10

Leu Cys Asn Gln Phe Ser Ala Ser Leu Ala Ala Asp Thr Pro Thr Ala
        -5                  1                   5                  10

Cys Cys Phe Ser Tyr Thr Ser Arg Gln Ile Pro Gln Asn Phe Ile Ala
                15                  20                  25

Asp Tyr Phe Glu Thr Ser Ser Gln Cys Ser Lys Pro Gly Val Ile Phe
                30                  35                  40

Leu Thr Lys Arg Ser Arg Gln Val Cys Ala Asp Pro Ser Glu Glu Trp
                45                  50                  55

Val Gln Lys Tyr Val Ser Asp Leu Glu Leu Ser Ala
        60                  65                  70

(2) INFORMATION FOR SEQ ID NO:24:

(i) SEQUENCE CHARACTERISTICS:
        (A) LENGTH: 96 amino acids
        (B) TYPE: amino acid
        (C) STRANDEDNESS: single
        (D) TOPOLOGY: linear

```
      (ii) MOLECULE TYPE: peptide (ix) FEATURE:
           (A) NAME/KEY: misc_feature
           (D) OTHER INFORMATION: "I-309"

(ix) FEATURE:
           (A) NAME/KEY: Protein
           (B) LOCATION: 1..73

(xi) SEQUENCE DESCRIPTION: SEQ ID NO:24:

Met Gln Ile Ile Thr Thr Ala Leu Val Cys Leu Leu Ala Gly Met
              -20              -15                 -10

Trp Pro Glu Asp Val Asp Ser Lys Ser Met Gln Val Pro Phe Ser Arg
     -5                    1            5

Cys Cys Phe Ser Phe Ala Glu Gln Glu Ile Pro Leu Arg Ala Ile Leu
 10              15                  20                      25

Cys Tyr Arg Asn Thr Ser Ser Ile Cys Ser Asn Glu Gly Leu Ile Phe
                 30                  35                  40

Lys Leu Lys Arg Gly Lys Glu Ala Cys Ala Leu Asp Thr Val Gly Trp
             45              50                  55

Val Gln Arg His Arg Lys Met Leu Arg His Cys Pro Ser Lys Arg Lys
             60              65                  70

(2) INFORMATION FOR SEQ ID NO:25:

(i) SEQUENCE CHARACTERISTICS:
          (A) LENGTH: 93 amino acids
          (B) TYPE: amino acid
          (C) STRANDEDNESS: single
          (D) TOPOLOGY: linear (ii) MOLECULE TYPE: peptide (ix) FEATURE:
           (A) NAME/KEY: Protein
           (B) LOCATION: 1..69

(ix) FEATURE:
           (A) NAME/KEY: misc_feature
           (D) OTHER INFORMATION:
               /note="The amino acid at position 24 is selected from the
               group consisting of arginine, glycine, alanine,
               valine, leucine, isoleucine, proline, serine,
               threonine, phenylalanine, tyrosine, tryptophan,
               aspartate, glutamate, asparagine, glutamine, cysteine,
               and methionine."

(ix) FEATURE:
           (A) NAME/KEY: misc_feature
           (D) OTHER INFORMATION:
               /note="The amino acid at position 27 is independently
               selected from the group consisting of lysine, glycine,
               alanine, valine, leucine, isoleucine, proline, serine,
               threonine, phenylalanine, tyrosine, tryptophan,
               aspartate, glutamate, asparagine, glutamine, cysteine,
               and methionine."

(ix) FEATURE:
           (A) NAME/KEY: misc_feature
           (D) OTHER INFORMATION:
               /note="The amino acid at position 30 is independently
               selected from the group consisting of tyrosine,
               serine, lysine, arginine, histidine, aspartate,
               glutamate, asparagine, glutamine, and cysteine."

(ix) FEATURE:
           (A) NAME/KEY: misc_feature
           (D) OTHER INFORMATION:
               /note="The amino acid at position 50 is independently
               selected from the group consisting of glutamic acid,
               lysine, arginine, histidine, glycine, and alanine."
```

(ix) FEATURE:
    (A) NAME/KEY: misc_feature
    (D) OTHER INFORMATION:
        /note="The amino acid at position 59 is independently
        selected from the group consisting of tryptophan,
        serine, lysine, arginine, histidine, aspartate,
        glutamate, asparagine, glutamine, and cysteine."

(ix) FEATURE:
    (A) NAME/KEY: misc_feature
    (D) OTHER INFORMATION:
        /note="The amino acid at position 60 is independently
        selected from the group consisting of valine, serine,
        lysine, arginine, histidine, aspartate, glutamate,
        asparagine, glutamine, and cysteine."

(xi) SEQUENCE DESCRIPTION: SEQ ID NO:25:

```
Met Ala Arg Leu Gln Thr Ala Leu Leu Val Val Leu Val Leu Leu Ala
            -20                 -15                 -10

Val Ala Leu Gln Ala Thr Glu Ala Gly Pro Tyr Gly Ala Asn Met Glu
         -5                   1                   5

Asp Ser Val Cys Cys Arg Asp Tyr Val Arg Tyr Arg Leu Pro Leu Xaa
         10                  15                  20

Val Val Xaa His Phe Xaa Trp Thr Ser Asp Ser Cys Pro Arg Pro Gly
 25                  30                  35                  40

Val Val Leu Leu Thr Phe Arg Asp Lys Xaa Ile Cys Ala Asp Pro Arg
             45                  50                  55

Val Pro Xaa Xaa Lys Met Ile Leu Asn Lys Leu Ser Gln
         60                  65
```

(2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

TATTGGATCC GTTCTAGCTC CCTGTTCTCC 30

(2) INFORMATION FOR SEQ ID NO:27:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

CCAAGAATTC CTGCAGCCAC TTTCTGGGCT C 31

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

GCGACTCTCT ACTGTTTCTC 20

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

```
CACAGGAAAC AGCTATGACC                                         20
```

(2) INFORMATION FOR SEQ ID NO:30:

(i) SEQUENCE CHARACTERISTICS:
        (A) LENGTH: 70 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
Leu Gly Pro Tyr Gly Ala Asn Met Glu Asp Ser Val Cys Cys Arg Asp
1               5                   10                  15

Tyr Val Arg Tyr Arg Leu Pro Leu Arg Val Val Lys His Phe Tyr Trp
            20                  25                  30

Thr Ser Asp Ser Cys Pro Arg Pro Gly Val Val Leu Leu Thr Phe Arg
        35                  40                  45

Asp Lys Glu Ile Cys Ala Asp Pro Arg Val Pro Trp Val Lys Met Ile
    50                  55                  60

Leu Asn Lys Leu Ser Gln
65                  70
```

(2) INFORMATION FOR SEQ ID NO:31:

(i) SEQUENCE CHARACTERISTICS:
        (A) LENGTH: 69 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

```
Gly Pro Tyr Gly Ala Asn Met Glu Asp Ser Val Cys Cys Arg Asp Tyr
1               5                   10                  15

Val Arg Tyr Arg Leu Pro Leu Arg Val Val Lys His Phe Tyr Trp Thr
            20                  25                  30

Ser Asp Ser Cys Pro Arg Pro Gly Val Val Leu Leu Thr Phe Arg Asp
        35                  40                  45

Lys Glu Ile Cys Ala Asp Pro Arg Val Pro Tyr Leu Lys Met Ile Leu
    50                  55                  60

Asn Lys Leu Ser Gln
65
```

(2) INFORMATION FOR SEQ ID NO:32:

(i) SEQUENCE CHARACTERISTICS:
        (A) LENGTH: 69 amino acids
        (B) TYPE: amino acid
        (C) STRANDEDNESS: single
        (D) TOPOLOGY: linear

```
    (ii) MOLECULE TYPE: peptide (xi) SEQUENCE DESCRIPTION: SEQ ID NO:32:

Gly Pro Tyr Gly Ala Asn Met Glu Asp Ser Val Cys Cys Arg Asp Tyr
1               5                   10                  15

Val Arg Tyr Arg Leu Pro Leu Arg Val Val Lys Glu Tyr Phe Tyr Thr
                20              25                  30

Ser Asp Ser Cys Pro Arg Pro Gly Val Val Leu Leu Thr Phe Arg Asp
            35              40              45

Lys Glu Ile Cys Ala Asp Pro Arg Val Pro Trp Val Lys Met Ile Leu
    50              55                  60

Asn Lys Leu Ser Gln
65
```